(12) United States Patent
Preston et al.

(10) Patent No.: US 10,093,941 B2
(45) Date of Patent: Oct. 9, 2018

(54) MODULATION OF FLAVONOID CONTENT IN CACAO PLANTS

(71) Applicant: CACAO BIO-TECHNOLOGIES, LLC, Brooklyn, NY (US)

(72) Inventors: Daniel Preston, Brooklyn, NY (US); Randall B. Murphy, Glenmoore, PA (US)

(73) Assignee: CACAO BIOTECHNOLOGIES LLC, Brooklyn, NY (US)

( * ) Notice: Subject to any disclaimer, the term of this patent is extended or adjusted under 35 U.S.C. 154(b) by 192 days.

(21) Appl. No.: 14/636,789

(22) Filed: Mar. 3, 2015

(65) Prior Publication Data
US 2016/0024515 A1  Jan. 28, 2016

Related U.S. Application Data

(63) Continuation of application No. 13/236,278, filed on Sep. 19, 2011, now Pat. No. 8,969,655.

(60) Provisional application No. 61/384,368, filed on Sep. 20, 2010, provisional application No. 61/387,149, filed on Sep. 28, 2010, provisional application No. 61/387,206, filed on Sep. 28, 2010.

(51) Int. Cl.
*A01H 5/00* (2018.01)
*C12N 15/82* (2006.01)

(52) U.S. Cl.
CPC ............... *C12N 15/8243* (2013.01)

(58) Field of Classification Search
CPC ............... A01H 5/10; C12N 15/8243
See application file for complete search history.

(56) References Cited

U.S. PATENT DOCUMENTS 7,109,033 B2 *  9/2006  Harper ............... C07K 14/415
                                                435/252.3
2009/0070899 A1 *  3/2009  Apuya ............... C12N 15/8255
                                                800/286

OTHER PUBLICATIONS

Liu et al. (Genbank Accession No. GU324351.1; Published Mar. 10, 2010).*
Liu et al. (Genbank Accession No. GU324352.1; Published Mar. 10, 2010).*

* cited by examiner

*Primary Examiner* — Vinod Kumar
(74) *Attorney, Agent, or Firm* — Duane Morris LLP

(57) ABSTRACT

Methods and materials for modulating (e.g., increasing or decreasing) flavonoid levels in *cacao* plants are disclosed. For example, nucleic acids encoding flavonoid-modulating polypeptides are disclosed as well as methods for using such nucleic acids to transform plant cells. Also provided are methods for accelerating breeding of *Theobroma cacao* plants of the porcelana variety with modulated levels of proanthocyanidin, its precursors and it polymers, useful in various medical and skin care products. Also provided are plants having modulated flavonoid levels and plant products produced from plants having modulated flavonoid levels.

28 Claims, 6 Drawing Sheets

Specification includes a Sequence Listing.

| Genotype | Catechins (mg/kg) | sd | Genotype | Epicatechins (mg/kg) | sd |
|---|---|---|---|---|---|
| 11 W | 1626.95 | 6.19 | 11 W | 52689.17 | 1518.27 |
| 11.2 W | 3601.91 | 96.30 | 11.2 W | 60937.31 | 791.00 |
| 12 W | 5691.08 | 515.59 | 12 W | 34805.58 | 3917.52 |
| 16.2 W | 2712.24 | 59.04 | 16.2 W | 35510.68 | 226.73 |
| 19 W | 4773.34 | 128.38 | 19 W | 66997.99 | 642.78 |
| 24 W | 3488.40 | 161.38 | 24 W | 57451.19 | 8913.22 |
| 32 W | 3365.48 | 199.32 | 32 W | 56852.47 | 1136.54 |
| 15 P | 3619.98 | 1646.69 | 15 P | 68515.68 | 9866.35 |
| 16.2 P | 5648.08 | 20.80 | 16.2 P | 76178.90 | 2447.82 |
| 18.2 P | 4103.91 | 205.57 | 18.2 P | 75957.79 | 7339.31 |
| 19 P | 3671.94 | 1079.64 | 19 P | 62244.33 | 129.14 |
| 23.1 P | 2443.08 | 1077.72 | 23.1 P | 67718.24 | 3384.47 |
| 24 P | 3801.02 | 327.68 | 24 P | 71845.96 | 7814.15 |
| 28 P | 1976.85 | 99.39 | 28 P | 22944.09 | 591.39 |
| 32 P | 4002.85 | 51.52 | 32 P | 79424.92 | 6809.74 |
| 9 P | 1829.42 | 66.56 | 9 P | 42346.29 | 3494.54 |
| 12 W/P | 7024.97 | 779.27 | 12 W/P | 45718.33 | 6946.08 |
| 9 W/P | 1507.40 | 310.51 | 9 W/P | 39711.49 | 2878.02 |

FIG. 5

MODULATION OF FLAVONOID CONTENT IN CACAO PLANTS

RELATED APPLICATIONS

This application claims the benefit of the filing date of U.S. Provisional Application No. 61/384,368, which was filed on Sep. 20, 2010; U.S. Provisional Application No. 61/387,149, which was filed on Sep. 28, 2010, and U.S. Provisional Application No. 61/387,206, which was filed on Sep. 28, 2010. For the purpose of any U.S. application that may claim the benefit of U.S. Provisional Application Nos. 61/384,368, 61/387,149 and 61/387,206, the contents of these earlier filed applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 30, 2011, is named Y4132020.txt and is 46,980 bytes in size.

BACKGROUND

Flavonoids are a diverse group of secondary metabolites that are synthesized in plants and have various biological functions. They are involved in plant defense against insects, pathogens and microbes and in absorption of free radicals and UV light. They also can act as pigments that attract beneficial symbionts and pollinators. Because the flavonoids are important for optimal plant growth and thus maximal agricultural productivity, the biochemistry and molecular biology of flavonoids is an important and very advanced area of research. Much of the knowledge in this field was reviewed by (Saslowsky, D., and Winkel-Shirley, B. (2001). Localization of flavonoid enzymes in Arabidopsis roots. Plant J 27, 37-48.; Winkel-Shirley, B. (2002). Biosynthesis of flavonoids and effects of stress. Curr Opin Plant Biol 5, 218-223.; Dixon, R. A., Xie, D. Y., and Sharma, S. B. (2005). Proanthocyanidins—a final frontier in flavonoid research? New Phytol 165, 9-28; Lepiniec, L., Debeaujon, I., Routaboul, J. M., Baudry, A., Pourcel, L., Nesi, N., and Caboche, M. (2006). Genetics and biochemistry of seed flavonoids. Annu Rev Plant Biol 57, 405-430). FIG. 1 shows an outline of the flavonoid biosynthetic pathway and a summary of biological functions of a few key metabolites. Enzymes involved in the pathway are listed in a sequential order (top to bottom): PAL, phenylalanine ammonia-lyase; C4H, cinnamate 4-hydroxylase; 4CL, 4-coumarate-CoA ligase; CHS, chalcone synthase; AS, aureusidin synthase; CHI, chalcone isomerase; FS1/FS2, flavone syntase; F3H, flavanone 3-hydroxylase; F3'H, flavonoid 3'-hydroxylase; F3'5'H, flavonoid 3',5'-hydroxylase; FLS, flavonol synthase; DFR, dihydroflavonol-4-reductase; LDOX (ANS), leucoanthocyanidin dioxygenase; LAR, leucoanthocyanidin reductase; ANR, anthocyanidin reductase; OMT, O-methyltransferase; UFGT, UDP-glucose:flavonoid 3-O-glucosyltransferase; RT, rhamnosyl transferase; C/EC refers to catechins/epicatechins, PPO refers to polyphenol oxydase.

Uses

The cocoa tree, Theobroma cacao, normally produces small amounts of epicatechin oligomers, commonly termed proanthocyanidins. These epicatechin oligomers are highly desired as they are potent antioxidants and thereby possess valuable properties as antioxidants, anti-inflammatories, and antiviral and antibacterial and antiparasitic agents. They have also been implicated in inhibition of low-density lipoprotein oxidation, vasodialation and reduction of hypertension, inhibition of platelet activation, and thus have many potential medical applications Hannum, S. M., and Erdman, J. W. (2000). Emerging health benefits from cocoa and chocolate. J Med Food 3, 73-75; Keen, C. L., Holt, R. R., Polagruto, J. A., Wang, J. F., and Schmitz, H. H. (2002). Cocoa flavanols and cardiovascular health. Phytochem Rev 1, 231-240; Fisher, N. D., and Hollenberg, N. K. (2005). Flavanols for cardiovascular health: the science behind the sweetness. J Hypertens 23, 1453-1459; Engler, M. B., and Engler, M. M. (2006). The emerging role of flavonoid-rich cocoa and chocolate in cardiovascular health and disease. Nutr Res 64, 109-118; Norman, K. H., Naomi, D. L. F., and Marjorie, L. M. (2009). Flavanols, the Kuna, cocoa consumption, and nitric oxide. J. Am. Soc. Hypertens 3, 105-112).

Enzymology

All flavonoids are derived from cinnamic acid, a derivative of the amino acid phenylalanine. Their biosynthetic pathways share some general steps and most start from the condensation of three malonyl-CoA units and p-coumaroyl-CoA catalyzed by chalcone synthase (CHS) to produce tetrahydroxychalcone. Yellow-colored tetrahydroxychalcone is then converted into the colorless naringenin through the stereospecific isomerization by chalcone isomerase (CHI) Dixon, R. A., and Paiva, N. L. (1995). Stress-induced phenylpropanoid metabolism. Plant Cell 7, 1085-1097; Holton, T. A., and Cornish, E. C. (1995). Genetics and biochemistry of anthocyanin biosynthesis. Plant Cell 7, 1071-1083). In legume species, tetrahydroxychalcone can also be reduced to trihydroxylchalcone by chalcone reductase (CHR), and then converted into liquiritigenin by CHI Welle, R., and Grisebach, H. (1989). Phytoalexin synthesis in soybean cells: elicitor induction of reductase involved in biosynthesis of 6'-deoxychalcone. Arch Biochem Biophys 272, 97-102).

Naringenin enters into different pathways as a substrate for the synthesis of six different groups of flavonoids. It can be converted into dihydroflavonols by flavanone 3-hydroxylase (F3H), flavonoid 3'-hydroxylase (F3'H) or flavonoid 3',5'-hydroxylase (F3'5'H). Dihydroflavonols can then be converted into flavonols by flavonol synthase (FLS) and anthocyanins by a series of enzymes including dihydroflavonol reductase (DFR), anthocyanidin synthase (ANS), UDP-glucose flavonol 3-O-glucosyl transferase (UFGT). Alternatively, naringenin can be converted by isoflavone synthase into isoflavones, which are the precursor for the synthesis of isoflavonoids. Naringenin can also be converted by DFR into flavan-4-ols, which are the precursors of 3-deoxyanthocyanidins, or it can be converted into flavones by flavone synthase 1 and 2 (FS1/FS2). One set of intermediates in the anthocyanin synthesis pathway, leucoanthocyanidins and 3-OH-anthocyanins are converted into the flavan-3-ols (catechin and epicatechin), which are polymerized into proanthocyanidins (condensed tannins) that are the major topic of this application.

Formation and Structures of Proanthocyanidins

The synthesis of proanthocyanidins (PAs) and anthocyanins shares common steps in the flavonoid biosynthesis pathway up to the synthesis of flavan-3,4-diols (such as leucoanthocyanidin), which not only are precursors for anthocyanin and flavan-3-ols synthesis, but also contribute to the extension units of the PA polymers (FIG. 1-2)(Dixon, R. A., Xie, D. Y., and Sharma, S. B. (2005). Proanthocyanidins—a final frontier in flavonoid research? New Phytol 165, 9-28). Flavan-3-ols (sometimes referred to as flavanols, such as catechin or epicatechin) derived from leucoanthocyanidins are believed to act as terminal units to initiate PA polymerization, while intermediates derived from leucoanthocyanidins themselves act as extension units to add to flavan-3-ol initiators through C4-C8 linkage (dominant form of PAs or C4-C6 linkage to form branches (not shown).

The hydroxylation pattern of the B-ring of the monomeric proanthocyanidins is determined by the presence of the cytochrome P450 monooxygenases flavonoid 3'-hydroxylase (F3'H) and flavonoid 3',5'-hydroxylase (F3'5'H), enzymes that act early in the flavonoid synthesis pathway after the formation of naringenin (Winkel-Shirley, B. (2002). Biosynthesis of flavonoids and effects of stress. Curr Opin Plant Biol 5, 218-223; Dixon, R. A., Xie, D. Y., and Sharma, S. B. (2005). Proanthocyanidins—a final frontier in flavonoid research? New Phytol 165, 9-28) (FIG. 1). In the absence of both of these cytochrome P450 enzymes, hydroxylation occurs only at the 4' position of B rings, yielding (epi)afzelechin. In the presence of F3'H, the 3' position will be hydroxylated resulting in the formation of (epi)catechin. In the presence of F3'5'H, the 5' position will also be hydroxylated leading to the formation of (epi) gallocatechin. The activity of F3'H and F3'5'H will also cause similar hydroxylation pattern on the B-ring of anthocyanins, resulting in the formation of pelargonidin with only one hydroxyl group, cyanidin with two hydroxyl groups, and delphinidin with three hydroxyl groups. The pigments derived from each anthocyanin have a characteristic color range since the visible absorption maximum becomes longer with the increase in B-ring hydroxyl groups: pelargonidin derived pigments show orange, pink or red colors, cyanidin-derived pigments show red or magenta colors and delphindin-derived pigments show purple or blue colors (Zuker, A., Tzfira, T., Ben-Meir, H., Ovadis, M., Shklarman, E., Itzhaki, H., Forkmann, G., Martens, S., Neta-Sharir, I., Weiss, D., and Vainstein, A. (2002). Modification of flower color and fragrance by antisense suppression of the flavanone 3-hydroxylase gene. Mol. Breed. 9, 33-41).

SUMMARY OF THE INVENTION

The invention features methods and materials related to modulating (e.g., increasing or decreasing) flavonoid levels in caco plants. The methods can include transforming a cacao plant cell with a nucleic acid encoding a flavonoid-modulating polypeptide, wherein expression of the polypeptide results in a modulated level of one or more flavonoids. Also featured are materials an methods for identifying individuals of *T. cacao* of the porcelana strain having unique proanthocyanidin profiles. Also featured are methods of identifying allelles of certain *T. cacao* genes that result in increased levels of flavonoids and methods of using these alleles to generate *T. cacao* plants having increased levels of flavinoids. *Cacao* plant cells produced using such methods can be grown to produce plants having an increased or decreased flavonoid content. Such plants may be used to produce, for example, foodstuffs having an increased nutritional content, and/or modified appearance or color, which may benefit both food producers and consumers, or can be used as sources from which to extract one or more flavonoids.

The details of one or more embodiments of the invention are set forth in the accompanying drawings, the description below, and/or the claims. Other features, objects, and advantages of the invention will be apparent from the drawings, descriptions, and claims.

BRIEF DESCRIPTION OF THE DRAWINGS

FIG. 5 is a table showing the levels of catechins and epicatechins in 15 different varieties of *cacao*.

DETAILED DESCRIPTION

Figure 1:
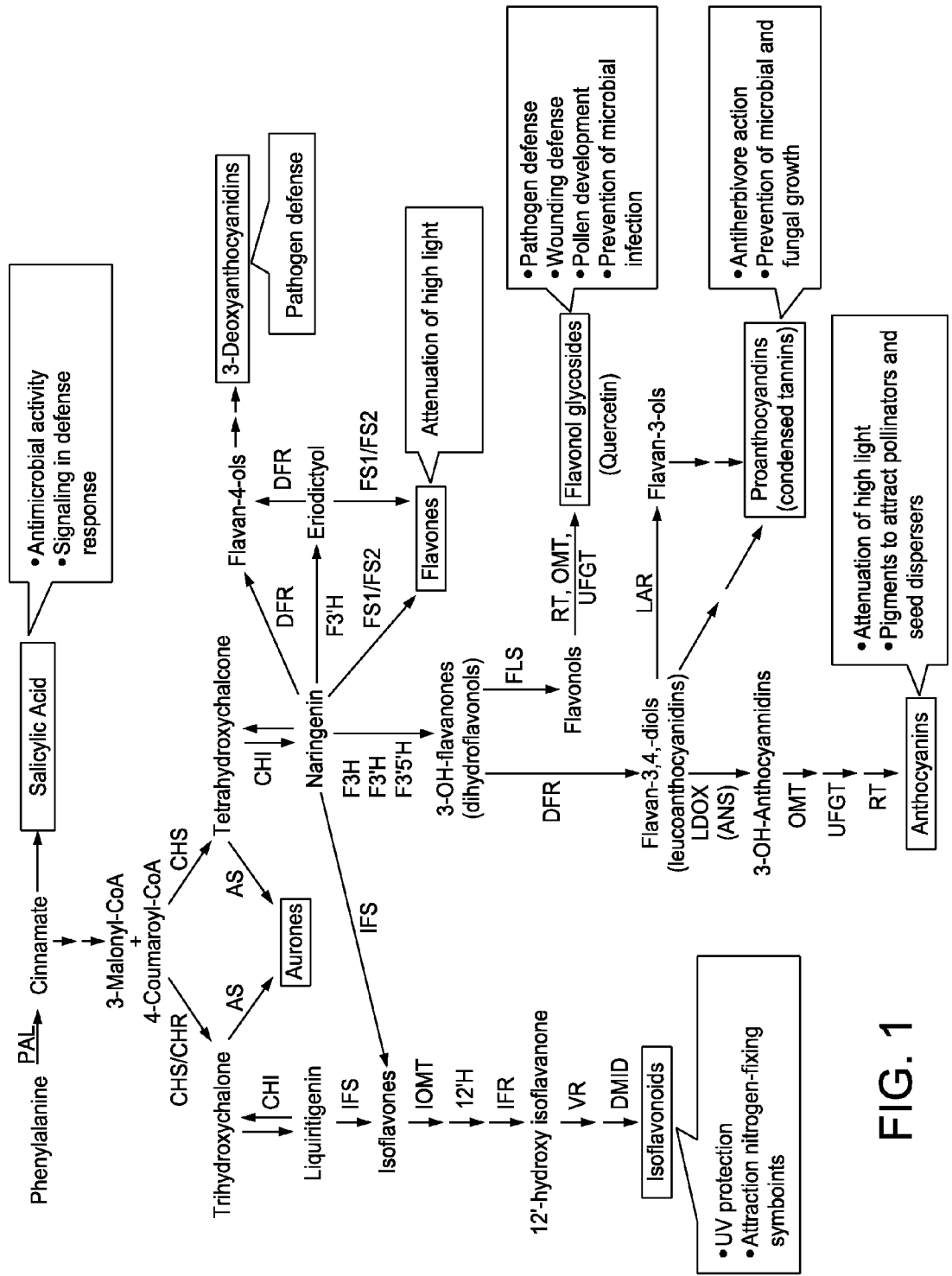
FIG. 1 depicts an outline of the flavonoid biosynthetic pathway and a summary of the biological functions of a few key metabolites.

We describe here novel genotypes of *cacao* of the porcelana strain with unique proanthocyanidin profiles and characteristics of utility. Furthermore we define DNA sequences (molecular markers) that will be used to detect alleles of genes encoding the key genes of the flavonoid pathway such that they will allow identification of individual plants containing alleles favorable for the synthesis of elevated and/or modified profiles of flavonoid metabolites. These markers will be specific to plants of the porcelana variety, known to have specific flavonoid characteristics advantageous to our applications.

We describe here DNA sequences (molecular markers) that will be used to detect alleles of genes encoding the key genes of the flavonoid pathway such that they will allow identification of individual plants containing alleles favorable for the synthesis of elevated and/or modified profiles of flavonoid metabolites. These markers will be specific to plants of the porcelana variety, known to have specific flavonoid characteristics advantageous to our applications. The present invention describes methods to develop molecular markers useful for accelerating the breeding of *cacao* plants with enhanced synthesis of flavonoids and includes the new varieties of *cacao* identified using the markers. The invention also comprises methods of combining multiple gene traits to achieve the altered synthesis desired.

Furthermore we define DNA sequences (molecular markers) that will be used to detect alleles of genes encoding the key genes of the flavonoid pathway such that they will allow identification of individual plants containing alleles favorable for the synthesis of elevated and/or modified profiles of flavonoid metabolites. These markers will be specific to plants of the porcelana variety, known to have specific flavonoid characteristics advantageous to our applications.

We describe here novel genotypes of *cacao* of the porcelana strain with unique proanthocyanidin profiles and characteristics of utility. We describe here DNA sequences (molecular markers) that will be used to detect alleles of genes encoding the key genes of the flavonoid pathway such that they will allow identification of individual plants containing alleles favorable for the synthesis of elevated and/or modified profiles of flavonoid metabolites. These markers will be specific to plants of the porcelana variety, known to have specific flavonoid characteristics advantageous to our applications. The present invention describes methods to develop molecular markers useful for accelerating the breeding of *cacao* plants with enhanced synthesis of flavonoids and includes the new varieties of *cacao* identified using the markers. The invention also comprises methods of combining multiple gene traits to achieve the altered synthesis desired.

Porcelana Variety of *Cacao*

Porcelana is a genetically pure genotype of the highly-prized and rare Criollo type of *cacao*, that is native to Venezuela and may have been grown there in the Pre-Columbian era. Porcelana cocoa was called "Maracaibo" in colonial times, since it was primarily exported from the Venezuelan port community. Along with a few other Mexican and Colombian cocoas beans, Maracaibo cocoa was classified as one of the world's highest quality cocoas until the 1920s. Today, many of these Mexican and Colombian cocoas have disappeared and have been replaced by more disease resistant hybrids. Maracaibo, or Porcelana cocoa is grown on small plantations in Venezuela.

The "Porcelana" variety of *T. cacao* is named as such because the cocoa beans are white in color as opposed to the normal brown color. We have discovered that Porcelana varieties contain substantial amounts of lower molecular weight epicatechin oligomers and low concentrations of high molecular weight epicatechin polymers. There is extensive evidence in the literature that proanthocyanidin profiles differ between different species and amongst different genotypes of a given species. In accordance, we have observed significant variation for the proanthocyanidins in *cacao*. The present invention will exploit the natural variation in the amounts and types of proanthocyanidins present in naturally occurring genotypes of *cacao*. These varieties have utility in that the concentrations, sizes and ratios of different polyphenol species are such that the resulting plant product, cocoa beans, will be an important source of molecules of pharmacological value. The added value will result from a combination of reduced processing costs, increased yields of biologically active ingredients, and enhanced specific activity of the ingredients due to optimized polymer profiles.

Genes Encoding the Enzymes in of the Flavonoid Pathway

Figure 2:
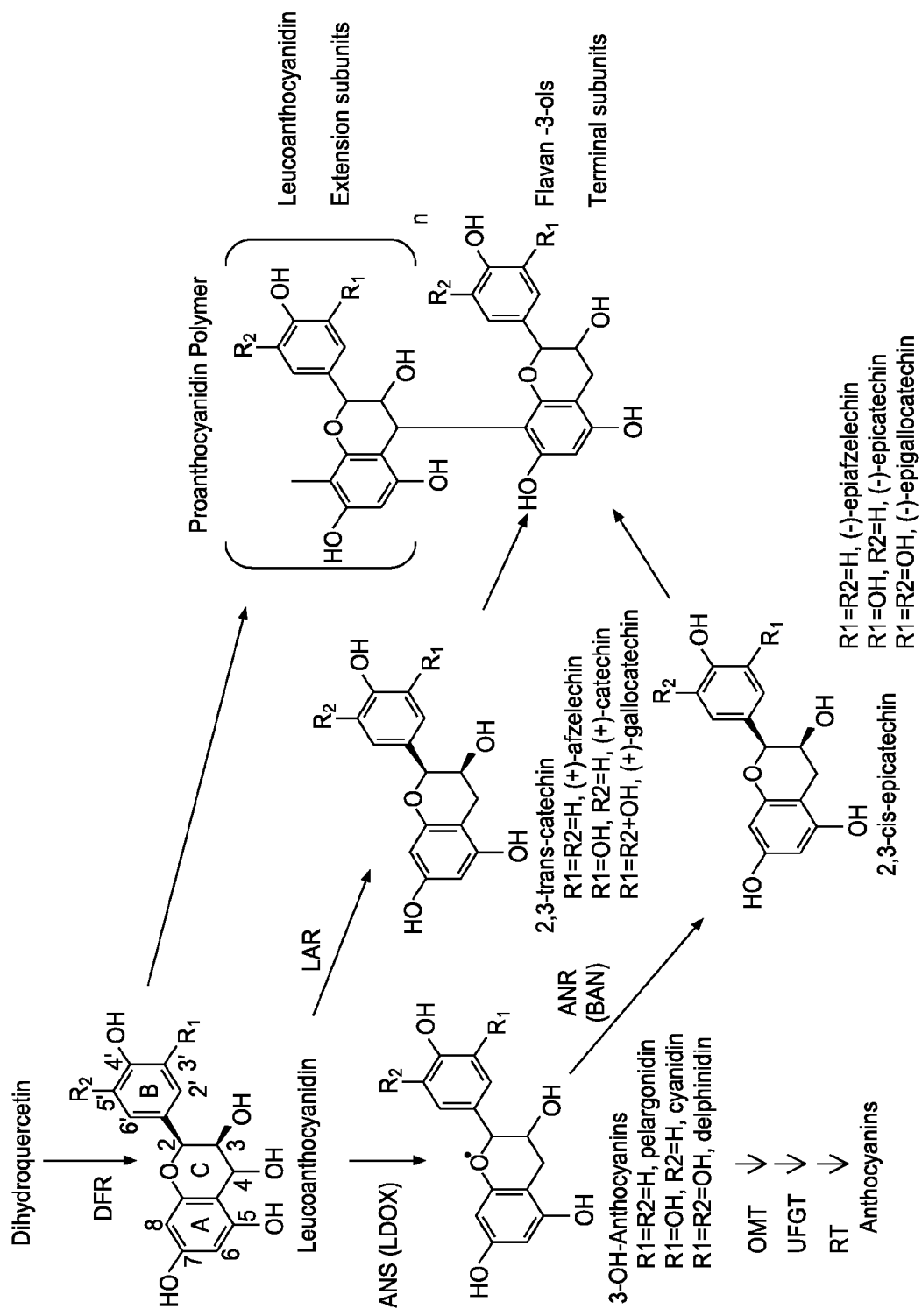
FIG. 2 depicts an outline of the details of proanthocyanidin synthesis pathway (adapted from Xie et al., 2003). Enzymes are represented in uppercase letters. DFR, dihydroflavonol 4-reductase, EC 1.1.1.219; ANS, anthocyanidin synthase, EC 1.14.11.19; ANR, anthocyanidin reductase, EC 1.3.1.77; LAR, leucoanthocyanidin reductase, EC 1.17.1.3; OMT, O-methyltransferases, EC 2.1.1.6; UFGT, UDP-glucose: anthocyanidin/flavonol 3-O-glucosyltransferase, EC 2.4.1.115; RT, rhamnosyltransferase, EC 2.4.1
Figure 3:
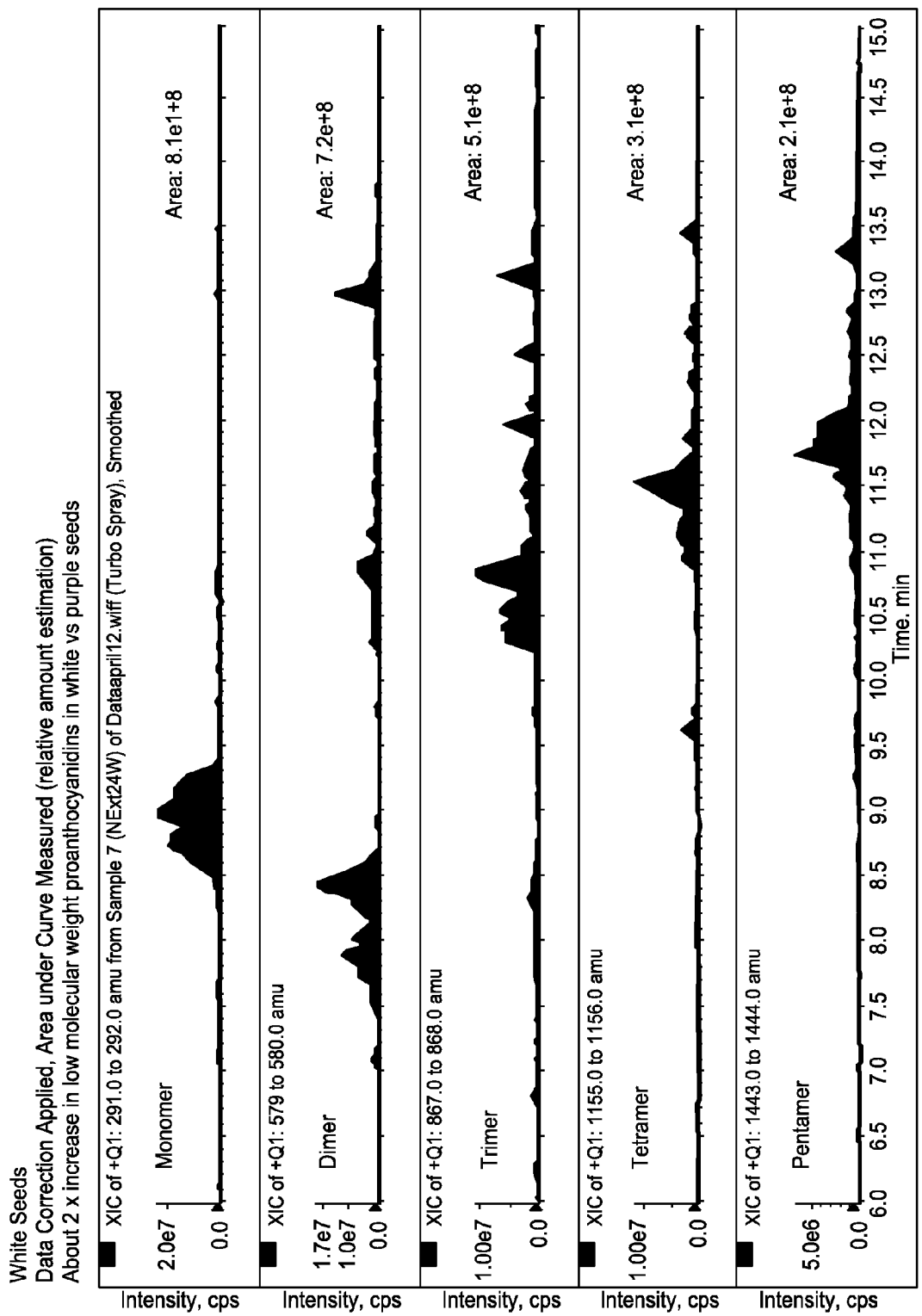
FIG. 3 shows the results of an LC analysis of proanthocyanidins in white seeds.

In higher plants, each of the enzymes of the flavonoid pathway are encoding by genes, in some cases multiple genes or gene families. The numbers of genes for each enzyme may differ in different species, but their sequences are highly conserved (greater than 50% sequence identity at the amino acid level). In the recent years, many genes regulating PA synthesis (transcription factors) have been cloned and characterized using mutants with reduced PA or anthocyanin content, (Marles, M. A., Ray, H., and Gruber, M. Y. (2003). New perspectives on proanthocyanidin biochemistry and molecular regulation. Phytochemistry 64, 367-383). The majority of these genes were cloned from *Arabidopsis* mainly due to the large collection of transparent testa (tt) transposon tagging or T-DNA insertion mutants. In *Arabidopsis*, PAs accumulate specifically in the innermost integumentary layer of the seed coat (endothelium) and will give the mature seed testa a brown color after oxidation Lepiniec, L., Debeaujon, I., Routaboul, J. M., Baudry, A., Pourcel, L., Nesi, N., and Caboche, M. (2006). Genetics and biochemistry of seed flavonoids. Annu Rev Plant Biol 57, 405-430). When genes required for normal PA synthesis are mutated, the mature seed will display a transparent testa phenotype (TT). The TT genes isolated to date include a basic helix-loop-helix (bHLH) transcription factor (TT8) (Alemanno, L., Berthouly, M., and MichauxFerriere, N. (1997). A comparison between *Theobroma cacao* L. zygotic embryogenesis and somatic embryogenesis from floral explants. In Vitro Cell. Dev. Biol. Plant 33, 163-172; Nesi, N., Debeaujon, I., Jond, C., Pelletier, G., Caboche, M., and Lepiniec, L. (2000). The TT8 gene encodes a basic helix-loop-helix domain protein required for expression of DFR and BAN genes in *Arabidopsis* siliques. Plant Cell 12, 1863-1878), a MYB transcription factor (TT2) (Nesi, N., Jond, C., Debeaujon, I., Caboche, M., and Lepiniec, L. (2001). The *Arabidopsis* TT2 gene encodes an R2R3 MYB domain protein that acts as a key determinant for proanthocyanidin accumulation in developing seed. Plant Cell 13, 2099-2114), a WD-40 repeat (WDR) protein (TTG1) (Walker, A. R., Davison, P. A., Bolognesi-Winfield, A. C., James, C. M., Srinivasan, N., Blundell, T. L., Esch, J. J., Marks, M. D., and Gray, J. C. (1999). The TRANSPARENT TESTA *GLABRA* 1 locus, which regulates trichome differentiation and anthocyanin biosynthesis in *Arabidopsis*, encodes a WD40 repeat protein. Plant Cell 11, 1337-1350), a MADS box gene (TT16, BSISTER) (Johnson, C. S., Kolevski, B., and Smyth, D. R. (2002). TRANSPARENT TESTA *GLABRA* 2, a trichome and seed coat development gene of *Arabidopsis*, encodes a WRKY transcription factor. Plant Cell 14, 1359-1375), a WRKY transcription factor (TTG2) ((Johnson, C. S., Kolevski, B., and Smyth, D. R. (2002). TRANSPARENT TESTA *GLABRA* 2, a trichome and seed coat development gene of *Arabidopsis*, encodes a WRKY transcription factor. Plant Cell 14, 1359-1375), and a new type of zinc finger protein (WIP) (TT1) Sagasser, M., Lu, G. H., Hahlbrock, K., and Weisshaar, B. (2002). *A. thaliana* TRANSPARENT TESTA 1 is involved in seed coat development and defines the WIP subfamily of plant zinc finger proteins. Genes Dev 16, 138-149) (FIG. 1-3). TRANSPARENT TESTA *GLABRA* 1 (TTG1) was the first anthocyanin regulator isolated in *Arabidopsis* through positional cloning (Walker, A. R., Davison, P. A., Bolognesi-Winfield, A. C., James, C. M., Srinivasan, N., Blundell, T. L., Esch, J. J., Marks, M. D., and Gray, J. C. (1999). The TRANSPARENT TESTA *GLABRA* 1 locus, which regulates trichome differentiation and anthocyanin biosynthesis in *Arabidopsis*, encodes a WD40 repeat protein. Plant Cell 11, 1337-1350).

Homologous Genes from *Cacao*

The model plant *Arabidopsis* and several other plant species are the main objects of research in this field from which all of the knowledge of these genes has been derived. Using these gene sequences from Arabodiopsis, populus and other plant species, sequences from *cacao* can be readily identified in the public database NCBI Genbank, using the publically available BLAST software and selecting gene sequences matching with evalues below 1*10-20. There are minimum of 159,996 *cacao* EST sequences in the NCBI database and representatives of each of the enzymes in the flavonoid pathway can readily be identified. These sequences were available prior to any release of whole genome sequence data into the public domain. The available sequences can be used to obtain full-length cDNAs and or genomic fragments by routine methods and to predict protein sequences from the gene sequences. Examples of the results of such analyses follow, all of the gene and protein sequences presented were obtained from the public NCBI database as described.

Sequences of *Theobroma cacao* Genes and Coding Sequences Encoding key Flavonoid Enzymes: NCBI Genbank Accession Numbers and annotation is given before each DNA sequence.

> gi|290579516|gb|GU324348.1|*Theobroma cacao* anthocyanidin reductase (ANR) complete cds (SEQ ID NO: 1)

ATGGCCAGCCAGACCGTAGGCAAAAAGACCGCTTGTGTCGTAGGTGGCACCGGATACGTT

GCATCTTTGTTGGTCAAGCTGTTGCTTGAGAAGGGCTACGCTGTTAACACTACTGTCAGG

GACCCAGACAACCAGAAAAAGATCCCTCACCTCGTAACACTACAAAAGCTAGGAGACTTG

AAAATCTTTCGAGCAGATTTGACTGATGAAGGCAGCCTTGATGTCCCCATAGCTGGTTGT

GACCTTGTCTTCCATGTTGCAACACCCGTCAATTTTGCTTCTCAAGATCCTGAGAATGAC

ATGATCAAACCAGCAATCCAGGGAGTGCTGAACGTTTTGAAAGCTTGTGCCAAAGCAAAA

ACAGTCAAACGGGTCGTCTTGACTTCTTCAGCCGCAGCTGTGTCTATCAACACACTCAAG

GGGACAGATCTGGTCCTGACTGAGAAAGACTGGACCGACGTTGAGTTCTTATCGTCGGCA

AAGCCACCAACTTGGGGGTACCCTGCATCCAAGACATTGGCTGAAAAGGCAGCATGGAAA

TTTGCTCAAGAAAACAACATCGATCTCATCACGGTCATCCCTTCTCTCATGACCGGTCCT

TCTCTCACCCCAGACGTGCCCAGCAGCATTGGCCTTGCCACATCTTTGCTTTCAGGCAAC

GAATTCCTTGTAAATGCTTTGAAAGGTATGCAAATGTTGTCAGGTTCAATCTCTATCACT

CATGTGGAGGACGTCTGTCGGGCCCATGTTTTTCTGGCAGAAAAAGAATCTGCATCCGGC

CGATATATATGCTGTGCTGTCAATTCCAGTGTTCCTGAGCTTGCTAAGTTCCTCAACCAA

AGATACCCTGAGTTCAAAGTCCCTACTGATTTTGGAGATTTCCCCTCTAAAGCCAAGTTG

ATCATTTCCTCGGATAAGCTTATTAATGAAGGATTCAGCTTTAAGTTTGGGATTGAGGAA

ATCTACGACCAAACTGTAGAATACATGAACGCTAAGGGGCTGCTCAAGTGA

ADD51354.1 GI:290579517 *Theobroma cacao* anthocyanidin reductase (ANR) amino acid sequence (SEQ ID NO: 2)

```
  1  masqtvgkkt acvvggtgyv asllvklllе kgyavnttvr dpdnqkkiph lvtlqklgdl
 61  kifradltde gsldvpiagc dlvfhvatpv nfasqdpend mikpaiqgvl nvlkacakak
121  tvkrvvltss aaaysintlk gtdlvltekd wtdveflssa kpptwgypas ktlaekaawk
181  faqennidli tvipslmtgp sltpdvpssi glatsllsgn eflvnalkgm qmlsgsisit
241  hvedvcrahv flaekesasg ryiccavnss vpelakflnq rypefkvptd fgdfpskakl
301  iissdkline gfsfkfgiee iydqtveymn akgllk
```

ADD51353.1 GI:290579515 *Theobroma cacao* anthocyanidin reductase (ANR) amino acid sequence (SEQ ID NO: 3)

```
  1  masqtvgkkt acvvggtgyv asllvklllе kgyavnttvr dpdnqkkiph lvtlqklgdl
 61  kifradltde gsfdvpiagc dlvfhvatpv nfasqdpend mikpaiqgvl nvlkacakak
121  tvkrvvltss aaaysintle gtdlvltekd wtdveflssa kpptwgypas ktlaekaawk
181  faqennidli tvipslmtgp sltpdvpssi glatsllsgn eflvnalkgm qmlsgsisit
241  hvedvcrahv flaekesgsg ryiccavnss vpelakflnq rypefkvptd fgdfpskakl
301  iissdkline gfsfkfgiee iydqtveymn akgllk
``` gi|290579514|gb|GU324347.1|*Theobroma cacao* anthocyanidin reductase (ANR) genomic sequence cds (SEQ ID NO: 4)

ATGCTCGATTGGCATGAAAAACACATCAAGCCCATGCACATTAAAGAAATGCGGAATATG

TCAAATTCTAAGACATGGATTCTCCACCATGGAGAAATCCAATGGTTTCCGGGGTGTTTT

TACATCTTCCATAGGTAAAAGAGCTTTAGAGTGTATTGAGCTTGATGAAGAGAACCGATG

TCTAAGAAAGGCTCTGGTAGTGTGCAGGGTAATTGCTGGAAGGGTTCAAAACCCTTTAGA

AAATGCGCAAGAAATGGCAAGTCAATCAAGCTTTGATTCACTGGCTGGAAACTTTGATAG

CCACTCGAATATTGAGGAACTCTATTCACTAAATCCTAGAGCTCTCTTCCCTTGTTTTGT

-continued

```
GGTCATCTGCAAACCCTCAAAGCAAAGTGCTCAAAAATTATAACTTAGGACCACGTTCCT

TGTCATTGTGATTGTGAGGTCTAATTTCTTTATCCAACCTTCTCTGTAATTATTTGTTCT

TATAGTAAATATATCTTCTCTTTCTGCAAGGTATTTGTTCTCTCAAAACTTCATCTTGAA

CCGCTATGAGATTGCATCAATCTACATAGAGCTGTAGCTAGTCTAGCTGCTTGAAGTTTC

TGACCAGCCTTCTCTTGCACCGCACCCTCTCTCTCTCCCCTCATTTTTCTAGTGAAAC

TGCCCCGAGGATTGAATTCTGTTCTGCAGATAAGTCAAATTTGACCATCAATCAAGCTCC

TATCCATTAATTCTGCTTGCTTATATCCCTTTTAGACAAATGTAATTAATAACACAAACC

CTAGTACAGAATCTATTAAGTCTAATTTGAATTCAATCCTGGAAGTGCACTGATCCTGCT

ATGCGTGGTCTAATTCGTCAACAACATTGTCCCCTCTTCTTTCTGTCTGCACTGTCTTGT

CACTACTATGGCTCTTCTTGGGCTCAGATCTAATCCTGATACTGTGTTTTGATAATAAGA

GTTGCTTACAGATACGAGTTAGGGTATTTAATTACAGACCTATTCGGGAAGGGGAAGGGA

AACTTGTTACAATGTACTTAACAAAGATCGTCAGGATATCTCCGGGTGTTCTTTGATCCT

CCTATGGGGTTAATCTTATGTTTCCTCGATTAAACAAATGAAAAATAAATAAATAAAGG

ATTCCTGGCAACAGTTCTCTGTTGCTTGCCTATAATTGAAATTGTGAATCATAAGAAGTA

AAACCACCTAACCACAGGCCCACGTGAGGCATCATTTGGAGCAACTTGAGGTTTGGCCAG

CTACCCCTCTTTTGCCTTCCAAAGATTTTAACTTGACATCAGTTGAGCCTTCACTTCCAA

CATTTCAGCAAACTTCATCTACTGTTTTTCTGCACCACTGCATGTCCTATATGATATCCA

AAAAACAACTCCCCCTTTCTAACATACAATAAATTTTGTGCTCGAAATCTGATTATCGCT

TATGATCATTACTGGAAGATGCCAAGCTCCAAAACTTCACCTAAATGCTTTTGTGTGCCT

CTTCTTAAGTCCATACTTTCTTAGTAAAAGAATGTGGATGCAAAAACCCATTTTGGGAAT

ACTTTTCCACAGTAAAAAAAAAAATTATTAGATTATGTCTTGATTCAATCAAAATTCCTC

AATGAACCATAGAACAATTTTAGTGACTAAAGCAGTTGATAAATACTCAACCCATTTACT

ATTATTTAATGGTTTTCTCATAGAACAATTTTTTAAGAAGTACACAAGCAATAAACTCTA

CATTTACTCTACATTTATCAATCGAATACAAAACTATATTTTGGTAGGGGGTCACTGTTA

ACTCAGTCATTATCAAAAGAAGCGATGAGAGGAAATGAGTTTCTAGCTAAAAAGAAACTC

GTGGGTACTGACTGGCTACCCCTTGTAGTAGCAGTTTGGGGAGTCGAGTCACACCACCGA

TGGTTTGAAAGACTTTTTGAGTCGTTGGTATGCACAAGGGCACGTGCTCACCTTCTCCAT

CTAAAAATCTACTCAAGCCCTGGGTAAGTGCCCATCGTCTATAAAACAATAATGCAATAA

GTTTATTCCACCTATGCATCTTTGTCTGAACGGTTGAAGGGTTCAAAACAAGCCCAAAAA

ATCGAAACGGAAAAGCAAAAGTAAGGTACCCGGTCAAGAAAAGGAATATAGTCATTGAAG

CCATGGCCAGCCAGACCGTAGGCAAAAAGACCGCTTGTGTCGTAGGTGGCACCGGATACG

TTGCATCTTTGTTGGTCAAGCTGTTGCTTGAGAAGGGCTACGCTGTTAACACTACTGTCA

GGGACCCAGGTTGATCTTCTCTTCTTCTTCATCTTCTTCTGTTTTTCTTGTTCATTTGTT

TCTACTGCTTTGCTTTGGTGGGTCATCCCAGTATTTTACTTTCTTCCCCTTCCTTGGTTT

TCTTGTTTTTATATATAATATATTGGTATGGCTGCTGCTGCAATTTAGGAATTTCTACGA

TTTATGCCCCCATTGTAGCATTAGTTCTTTGTTCTTTGTTTTTCACTTTAAGCTTAAAC

TATAAATTCCTACCTACTCTGTATCGAGCATGTTGGAAGTTAATAAGCGAGAACAACCGA

GGAACATACCGCCTTGTCTTGTCAGTTGGTGTTTTTAGGGGGTACCCACGATATCCGTT

GCCTGAGCAGGAGAGAATACTATCAATTCCTTGGGTTTGAGTTCACCCCTCTCGAAGAGT

TTCCTTACCAAATTAATCACATTTTTTGCAGATAAAGTGTAATGAGTAGAATCTTTTTTT
```

-continued

```
CTTTTTTCTTTTTGGGGGTTTATTTTCATTTTCTGGCAACACCCAGAGTAAGTAAACATG

AATGGGTGTAATGCTGTGTCTTTTCTGCAGACAACCAGAAAAAGATCCCTCACCTCGTAA

CACTACAAAAGCTAGGAGACTTGAAAATCTTTCGAGCAGATTTGACTGATGAAGGCAGCT

TTGATGTCCCCATAGCTGGTTGTGACCTTGTCTTCCATGTTGCAACACCCGTCAATTTTG

CTTCTCAAGATCCTGAGGTATGTAAAACCATTAAACTGCTTTTCCAGTGATGATCAAATT

CCTTCTGGTTTTGAGGAATGATGACAAGGTTTACTTTATTGGATTTTGATTATAGAATGA

CATGATCAAACCAGCAATCCAGGGAGTGCTGAACGTTTTGAAAGCTTGTGCCAAAGCAAA

AACAGTCAAACGGGTCGTCTTGACTTCTTCAGCCGCAGCTGTGTCTATCAACACACTCGA

GGGGACAGATCTGGTCCTGACTGAGAAAGACTGGACCGACGTTGAGTTCTTATCGTCGGC

AAAGCCACCAACTTGGGTAACAATTTTCATGCTAATCCATTCCTCTTTCTCTTATCTTCG

GGGGAATTGCAGAAGAGGGCAAGGTAACAAAAATAATTGGTGTGCATAATCTGAAGTAAG

CTTTTATCCATGAATGCAGGGGTACCCTGCATCCAAGACATTGGCTGAAAAGGCAGCATG

GAAATTTGCTCAAGAAAACAACATCGATCTCATCACGGTCATCCCTTCTCTCATGACCGG

TCCTTCTCTCACCCCAGACGTGCCCAGCAGCATTGGCCTTGCCACATCTTTGCTTTCAGG

TATTAAGTTAGAACCTCGTGTCCTGGCCTTGTTTCTAGATGTAAAACTGATGCATAAAGA

AGTAGCCTGGAGCACCATGAACTGTAACTGATGGGAATTTTAACATTTTTGCAGGCAACG

AATTCCTTGTAAATGCTTTGAAAGGTATGCAAATGTTGTCAGGTTCAATCTCTATCACTC

ATGTGGAGGACGTCTGTCGGGCCCATGTCTTTCTGGCAGAAAAAGAATCTGGATCCGGCC

GATATATATGCCTGTGCTGTCAATTCCAGTGTTCCTGAGCTTGCTAAGTTCCTCAACCAA

AGATACCCTGAGTTCAAAGTCCCTACTGAGTAAGCCAACCTGCATTCAATATCACAATCT

AAACTTCTCTTCTTTCTGCTAGAATTGTGGTTAATCTTAGTTTTGTTTGCTTTGTTACAA

TTGCAGTTTTGGAGATTTCCCCTCTAAAGCCAAGTTGATCATTTCCTCGGATAAGCTTAT

TAATGAAGGATTCAGCTTTAAGTTTGGGATTGAGGAAATCTACGACCAAACTGTAGAATA

CATGAACGCTAAGGGGCTGCTCAAGTGAAGAGTCCGCCTAACATTGTCCCTAATGACTGT

GATGTTTGGTTGCTTAAGATGTATGCTGTCTTTTGTTATATTATCCTAATAACTTGATGT

TCTGCAAATCAAGCAAATACCATATGGCGAATATCATTTGCTTTCCCAAAAGAAAAAGAA

AAAAAAAAAGAAATCCAAAGTATCCTATTTAGTATTGGAAGACCAAAAATCAAATCACC

AACTGAATCATGGAATGGGTTCTTGTGTACTTATCAAATGACTATCATACTTTCCTTCTG

CGTCCAATTCTTCAACGTTCAATTAAAGAAGGATCAACAGTCCCTTGTAGATCCAGTTTG

AAAGTTGATCTTCAAAAAAAAAAAAATCCAGTTTGAAAGTAGTTTCCTCTGCTTTAGCAG

GTGGTTTTGCCCATGTTGCACCCTTGAGTTTCTTGGCTTGTGGGTCTCGGACAATGTCAG

CACGATGTCCCTCATTGAGGGCCTTTTCCTGGAGACAGGATTGATACAAGTATAAGCAAG

GGCAGCCATATGATTCAGTTGTTGAACATCAAATGTTCCTTGAAGTCGAGGATCTGCAAT

CTCTTCCCACCCTACATCGTTTTCCACATCAATAGCCGCCTATTCATGATCACAGAAACA

AGAAAAATGATATTGAATCATTCATGTTTTGTGCATGCATAGGCACTCAAAATCAGGTGA

GCAAAGAGCAGA
``` gi|290579520|gb|GU324350.1|*Theobroma cacao* anthocyanidin synthase (ANS) complete cds (SEQ ID NO: 5)

```
ATGGTGACTTCAATGGCCCCCAGAGTAGAGAGCTTGGCAAGCAGTGGGATTCAGTCCATC

CCGAAGGAGTACATTAGACCTCAGGAAGAGCTTACAAGCATTGGTAATGTGTTTGAAGAA

GAGAAAAAGAGGAAGGGCCTCAGGTTCCAACCATTGATTTAAAGGAAATTGACTCAGAG
```

-continued

```
GACAGAGAGGTACGGGAGAGATGTCGCCAGGAGTTGAAGAGAGCTGCCACGGAGTGGGGT

GTGATGCACCTTGTTAACCATGGGATCTCGGACGAGCTCATGGAACGTGTCAAGAAAGCT

GGACAGAAGTTCTTTGAACTTTCTGTCGAGGAGAAAGAGAAGTATGCCAACGACCAGACT

TTGGGGAAGATTCAGGGGTATGGCAGCAAGCTAGCTAACAATGCTAGTGGTCAGCTTGAG

TGGGAGGACTACTTCTTCCATCTTGTGTATCCCGAGGACAAGAGAGACTTGTCCATCTGG

CCTCAAACACCAAGCGACTACACTGAAGTCACAAGTGAGTACGCAAGGCAACTCCGAGTC

CTTGCGAGCAAAATTCTTTCGGCACTATCACTTTGCTTAGGATTGGAAGAAGGAAGGCTA

GAGAAGGAAGTTGGTGGATTGGAAGAGCTCCTTCTTCAAATGAAAATCAATTACTATCCC

AAATGCCCTCAACCAGAACTCGCTCTCGGTGTGGAAGCTCACACAGATGTAAGTGCACTT

ACCTTCATTCTCCACAACATGGTCCCTGGCCTGCAACTTTTCTACGAAGGCAAGTGGATC

ACCGCAAAATGTGTTCCAAACTCCATCATCATGCACATTGGTGACACCGTCGAGATCCTC

AGCAATGGTAAGTACAAGAGCATTCTTCACAGGGGTCTGGTTAACAAGGAGAAGGTTAGG

ATCTCATGGGCAGTTTTCTGTGAGCCGCCAAAGGAGAAGATCATTCTCAAGCCACTGCCA

GAGACTGTGTCCGAGACGGAGCCTCCGTTGTTCCCTCCTCGCACCTTTGCTCAGCATATT

CACCACAAGCTGTTTAGGAAGACCCAGGATGGCCTGTCTAATTGA
```

ADD51356.1 GI:290579521 *Theobroma cacao* anthocyanidin synthase (ANS) amino acid sequence.

(SEQ ID NO: 6)

```
  1   mvtsmaprve slassgiqsi pkeyirpqee ltsignvfee ekkeegpqvp tidlkeidse
 61   drevrercrq elkraatewg vmhlvnhgis delmervkka gqkffelsve ekekyandqt
121   lgkiqgygsk lannasgqle wedyffhlvy pedkrdlsiw pqtpsdytev tseyarqlry
181   laskilsals lclgleegrl ekevggleel llqmkinyyp kcpqpelalg veahtdvsal
241   tfilhnmvpg lqlfyegkwi takcvpnsii mhigdtveil sngkyksilh rglvnkekvr
301   iswavfcepp kekiilkplp etvseteppl fpprtfaqhi hhklfrktqd glsn
```

ADD51355.1 GI:290579519 *Theobroma cacao* anthocyanidin synthase (ANS) amino acid sequence.

(SEQ ID NO: 7)

```
  1   mvtsmaprve slassgiqsi pkeyirpqee ltsignvfee ekkeegpqvp tidlkeidse
 61   drevrercrq elkkaatewg vmhlvnhgis delmervkka gqkffelsve ekekyandqa
121   lgkiqgygsk lannasgqle wedyffhlvy pedkrdlsiw pqtpsdytev tseyarqlry
181   laskillals lclgleegrl ekevggleel llqmkinyyp kcpqpelalg veahtdvsal
241   tfilhnmvpg lqlfyegkwi takcvpnsii mhigdtieil sngkyksilh rglvnkekvr
301   iswavfcepp kekiilkplp etvseteppl fpprtfaqhi hhklfrktqd glsn
``` gi|290579518|gb|GU324349.1|*Theobroma cacao* anthocyanidin synthase (ANS) genomic sequence (SEQ ID NO: 8)

```
TATATATATATATATATATATATATATATATATATATATATATATATATTGTGTGG

AAAAACTAAAAGGCTTTTACTCTTCTGGTCAAGAACAAGAAGAATGGGCAAGCACCAAAA

AAGCAAAAAAGTCTTTGTTCCCCTTCTTTTGTTCGACCTGTTTATCCCATAGTTCATATA

AAATCACATTTTTGGCCAATTTTTTAGGGACGAAGAAACAAGGAACGGAGGCCAAGGCAA

GATAGGGGCCGGTGGTTTTGCTAGCAAATACATACGAAAATTAATTGAACTAGGTAGCAG

CAGGCATATATCCTGCTGACTGAAAGCTCGTAGAGATGAAGCACGAGCAACCAACTACCT

CATTGTTCTTCCAGAAGCAACTCCTAGTTTCGATCCCATGCAAGATCTTCAATCATATAA

CGTCTAGAACTTTCTTCTTTCGTACATAATAAGTAATGTTCAAAATCAACCATTTGTTAA

AAGCAAAACCATATGGAATAATATTGAATTAAACCTATTTAAATTTCAATTGAAGCTTTT
```

-continued

```
TTCGGAATGAATGGTCCATAAACTAGACTTTCTAATGCTTAGACTAACAAGGTGTATATA
TATATATATGTTAAGAGTATATAATTTTGATCATTTTTATTCGTTATTAAAAATATATTT
TACAAGTTTTATTACTTTATAATATATAATATAAAACGAAAGGAGTATTATTATTCATAA
AAAAAAGAAATCCAATTCTCATCTCATCTATGCATTGTTGAGTCAAGGCCTTAATGTTTT
TTGAGTTCAATCAAACTTTAATGTTTCCAAAAAGAGGGCAGGGGAGGGATTCAATTAACT
CCGCTAATGATGATTAGCTGTTGAAATCATTTGAGTCCTCTCTGCCATTTGGGGTTAAAT
GAATCCAAATTAAGATGGGTTAGATGAAACGTGCAGTCCTGGCTTGGTAGTTGGACTTTC
CAAGTAGAAATTTTGGTCGTTATTTATCCGCGCTCTGCTTAATTAATTAGTCAACTCTCC
TGTAAAGCAAATCAGCTAATTTGCTTAAACTACCCATTACTACTATGTACATTAGCTCAA
GAAATGTGCACTTTAGGCATTGCTCCATTGCCTGGTGTAAATTAAGTTAAAGTACAAAGT
GACTTAATAGAAAGAGTGTTTATTATGACATTATTAATACTTTTAATTTCTCTCAAATAA
CATTATTTAAGACATGGATAATTAACTTTTATGTATGTATAATCTTTTCATTTTATAAAA
GTTAAACCATTGATAAACAGGTTATCTAGCATGGTTCAAAAAAACAGTAAGTAATTTAGA
ATAGTACAATTTAATATTTAAATTAAGAGATATTGAAAACTTATATAGTATTAGATGTAT
ATATTGAACATTAATTACTTGTTGAATGGATGTTTTCATTTTTACATATAATTTTAGGTT
CACAAGAATTATATGATGAATGGAAAAGAAACAAAAGCAAAACAAGTTCTACCTCACAGG
CGCGTTTGGTTGAGATAGATTAGCAAATTAGAGCAGAGGGTGTTAGGTCCAAGCTTCCAG
TCAACTCACCTTGGGACAACCAAAGTTGTATGACCACTGCTCTAACTCAGACCTTGGTGG
AGCTCATCACGTGTATGACTTACCAGTTACATCTATTTTTCTTCAGTATTTCTTTCTCTT
GATTTGGTAGCTCTACCCCATTTGCATGTTCACTAAGGCAACTGATTTTTTTTTTTTTTA
ATATCATAGCTTTCTTGATCTTCCGTGTTAAAATTTTCTCGAACCAGATCATTATAAAAA
GGCCACTAAAGATCAGCACTACGGTATATTCCTGAGAGTGAGGTTCACCACAAAAGCAAA
AAAAAAAAAAAGGGTTGTTGTTACAGAGTGGAAACAAGGAACTTCTAAAACAAGTTTAG
AAGATCGCAAGAATGGTGACTTCAATGGCCCCCAGAGTAGAGAGCTTGGCAAGCAGTGGG
ATTCAGTCCATCCCGAAGGAGTACATTAGACCTCAGGAAGAGCTTACAAGCATTGGTAAT
GTGTTTGAAGAAGAGAAAAAAGAGGAAGGGCCTCAGGTTCCAACCATTGATTTAAAGGAA
ATTGACTCAGAGGACAGAGAGGTACGGGAGAGATGTCGCCAGGAGTTGAAGAAAGCTGCC
ACGGAGTGGGGTGTGATGCACCTTGTTAACCATGGGATCTCGGACGAGCTCATGGAACGT
GTCAAGAAAGCTGGACAGAAGTTCTTTGAACTTTCTGTCGAGGAGAAAGAGAAGTATGCC
AACGACCAGGCTTTGGGGAAGATTCAGGGGTATGGCAGCAAGCTAGCTAACAATGCTAGT
GGTCAGCTTGAGTGGGAGGACTACTTCTTCCATCTTGTGTATCCCGAGGACAAGAGAGAC
TTGTCCATCTGGCCTCAAACACCAAGCGACTACACGTGAGTTTATGGCTTTTGGTTTATT
TTACATACTGCTTTTTGCAATTACTAGATTCTTTGATCGATTAATGTTAATGTTTCTTGA
GCATCATATCAAACAAGCTGTATATGTCCACCGGGTTCATTGAACACTATCACAATTTTT
TTTTTAAAAGTGAAAACTTTCACATTTAATAAAAAGATCTACAAGGTTGGCAATTATCTG
TCTGCCTGATTAGATAGAAAATTTTCCTAATATTCAGGATACTTATTACAGTAAGAACAA
TATTTCTGTGATATGAAATATTAAAGTTAAACGTAAACTATCCGTATGGATTTTAACAAT
TCACCACTGTTCATTGGTTACTATGCAGTGAAGTCACAAGTGAGTACGCAAGGCAACTCC
GAGTCCTTGCGAGCAAAATTCTTTTGGCACTATCACTTTGCTTAGGATTGGAAGAAGGAA
GGCTAGAGAAGGAAGTTGGTGGATTGGAAGAGCTCCTTCTTCAAATGAAAATCAATTACT
ATCCCAAATGCCCTCAACCAGAACTCGCTCTCGGTGTGGAAGCTCACACAGATGTAAGTG
```

-continued

```
CACTTACCTTCATTCTCCACAACATGGTCCCTGGCCTGCAACTTTTCTACGAAGGCAAGT

GGATCACCGCAAAATGTGTTCCAAACTCCATCATCATGCACATTGGTGACACCATCGAGA

TCCTCAGCAATGGTAAGTACAAGAGCATTCTTCACAGGGGTCTGGTTAACAAGGAGAAGG

TTAGGATCTCATGGGCAGTTTTCTGTGAGCCGCCAAAGGAGAAGATCATTCTCAAGCCAC

TGCCAGAGACTGTGTCCGAGACGGAGCCTCCGTTGTTCCCTCCTCGCACCTTTGCTCAGC

ATATTCACCACAAGCTGTTTAGGAAGACCCAGGATGGCCTGTCTAATTGAGGCTAGTCAT

TAGTTAAATTAAAAATATCTTCTTGTTTTTAACGTCTTTATAAGCTGTTTACGGGTCTGG

TGATGCTATATTATCTTGGGTTAAACCTTTGGTTGTGGTAGGCTGATGCCGGGGTGGTGT

CTGTCTTTCACTCCTTGGCTTCTCTTTACCTGCTTTATTGAATAATGGCAGACTGATTTG

CTTCCTTGTGTTAAGCAGTTTGTGAATTAATGGTCTTTGTTTACATTTCTTTCCTCAATT

TACGTCTCCATAAACAGAACTCTTTCCCCTCCACACTTTCCTTCTTAGTCTAAATTTTTT

AATACAATAGCAATCTTTTTCTTAAACAAATCAAGTGAAGTACCTGTAATTATCTAAGTA

GTGAATCAAACCCTAAACAGGCAAGTTTTTGCCTCCCTTCCGTTCTTTTTATTCCGAACA

CCCAGGAAATTAACAAAAGGTAAATTGTCCCCAGTGGCACTCGGTTAATTGTCGTTTAGA

TTTTGATATGTATAACTTTGTGTTGGGGGCATTTTCTGCCCTGTGAAGGTCAAGCAGCCA

TGCTAACAGTATAACTATTAAGTAGTCTCAATAATGAAG
``` gi|290579524|gb|GU324352.1|*Theobroma cacao* leucoanthocyanidin
reductase (LAR) complete cds
(SEQ ID NO: 9)

```
ATGGATATGAAATCAACAAACATGAATGGTTCCTCTCCTAATGTCTCGGAAGAAACTGGT

CGGACCTTAGTCGTTGGTTCGGGTGGGTTTATGGGCCGGTTCGTCACCGAAGCCAGCCTA

GACTCCGGCCGTCCTACGTATATTTTGGCTCGGTCTAGTTCGAACTCTCCTTCCAAAGCC

TCCACCATCAAGTTTCTTCAAGACAGAGGAGCCACTGTTATTTACGGCTCTATCACAGAC

AAAGAATTCATGGAGAAGGTTCTGAAAGAACATAAGATAGAAGTTGTAATATCTGCAGTG

GGAGGGGGAAGCATCTTAGACCAGTTCAATCTGATAGAGGCTATCAGGAATGTTGACACT

GTCAAGAGGTTCTTACCGTCTGAATTCGGGCACGACACAGACAGGGCTGACCCGGTGGAG

CCAGGGCTGACCATGTATGAACAAAAGAGGCAGATTAGGAGGCAGGTAGAGAAATCTGGG

ATTCCTTACACTTACATATGTTGCAATTCCATTGCAGCTTGGCCCTACCACGACAACACT

CACCCTGCAGATGTTCTGCCACCCCTTGATAGGTTCAAAATATACGGTGATGGCACTGTC

AAAGCATACTTTGTGGCGGGTACCGATATTGGGAAGTTCACTATAATGTCGATAGAAGAT

GATCGAACACTGAACAAAACTGTCCATTTTCAACCTCCAAGCAACCTACTAAACATAAAC

GAGATGGCCTCACTATGGGAGGAGAAGATTGGACGTACACTTCCTAGGGTCACCATCACA

GAAGAAGATCTGCTGCAGATGGCCAAAGAGATGCGGATCCCACAGAGTGTGGTTGCAGCA

TTAACTCATGATATTTTCATAAATGGCTGCCAAATAAACTTTAGCTTGGACAAGCCAACT

GATGTTGAAGTCTGCTCCCTCTACCCAGACACTCCTTTTCGAACCATCAACGAGTGCTTC

GAGGACTTTGCCAAGAAGATAATTGATAATGCCAAAGCAGTGAGCAAGCCAGCGGCAAGC

AACAATGCAATATTTGTGCCAACTGCTAAGCCAGGAGCATTGCCTATCACTGCGATATGC

ACATGA
```

ADD51358.1 GI:290579525 *Theobroma cacao* leucoanthocyanidin
reductase (LAR) amino acid sequence
(SEQ ID NO: 10)

```
  1  mkstnmngss pnvseetgrt lvvgsggfmg rfvteaslds grptyilars ssnspskast
 61  ikflqdrgat viygsitdke fmekvlkehk ievvisavgg gsildqfnli eairnvdtvk
```

-continued

```
121    rflpsefghd  tdradpvepg  ltmyeqkrqi  rrqveksgip  ytyiccnsia  awpyhdnthp 181    advlppldrf  kiygdgtvka  yfvagtdigk  ftimsieddr  tlnktvhfqp  psnllninem 241    aslweekigr  tlprvtitee  dllqmakemr  ipqsvvaalt  hdifingcqi  nfsldkptdv 301    evcslypdtp  frtinecfed  fakkiidnak  ayskpaasnn  aifvptakpg  alpitaict
```

ADD51357.1 GI:290579523 *Theobroma cacao* leucoanthocyanidin
reductase (LAR) amino acid sequence (SEQ ID NO: 11)

```
  1    mkstnmngss  pnvseetgrt  lvvgsggfmg  rfvteaslds  grptyilars  ssnspskast 61    ikflqdrgat  viygsitdke  fmekvlkehk  ievvisavgg  gsildqfnli  eairnvdtvk 121    rflpsefghd  tdradpvepg  ltmyeqkrqi  rrqieksgip  ytyiccnsia  awpyhdnthp 181    advlppldrf  kiygdgtvka  yfvagtdigk  ftimsieddr  tlnktvhfqp  psnllninem 241    aslweekigr  tlprvtitee  dllqmakemr  ipqsvvaalt  hdifingcqi  nfsldkptdv 301    evcslypdtp  frtinecfed  fakkiidnak  ayskpaasnn  aifvptakpg  alpitaict
``` gi|290579522|gb|GU324351.1| *Theobroma cacao* leucoanthocyanidin
reductase (LAR) genomic sequence (SEQ ID NO: 12)

```
TGAGCAGCACTGATGTAAATTAAAAAAAGTTTAGGACTAATAAAAAAATTCATTCAAAAA

ATTTGGTAAAATAACAAAAAATTTACCATATGACTTGAAGACGAAAAAAATTTGTTTTCA

AAAATCAAACTCCATGTGACCCAAGAATCATAATAAAATCCCTATTAATAATGATTCTCA

CTTTTAATTTAAAAAAAAAAAACCAACACTCTATATGTAAGATAGATGATAAAATTTGAT

TAATTCAATCTCACATGTTGGGACTAGTAAATTCCATAAGATAATATGATTCCTTTCTGA

CAACCAATCAGGAAGAATTTCAATCAATTTTTGCTTAATAAAAAAAGATTATCCTGTCTG

CCATTGTTGTCAGAGGGTTTTTTTTTTTCACAGTTTAAGATCTATGTTTTATATAATTA

ATGAGGCCATTCTTCTATATATATATATATATATGGAGTACTTGCACTAATTTAATCT

CATTTAAATTTTAATTTACTAAAAAGTATATATTAATTTTGGTCCATGCCTGCACAACA

AAAAATATTATTTCTAAATTATATCGATAATTACAATTTACAAAGCTAAAATAAAATAAA

ATAAAAATTAAATTAAAAGCCTATTTGGTTTGATTTTTTAAAACTTAAAAATTAATATA

AAACTCTTATGAAAAATAATAGCTTTCAAAATTAAGTTAAATCTGTTTGGTAAATTTACT

TTTATAAGCTCTATTTTATAGATAAGTTGTTTTGCAAACAATTTATATAAGTTTTAATT

TTAGTTAAAATTACAATCAAGGGTGTGTGTAATAAATAACTTTTTATTAATCATAAATTT

TTTTTAGAACAATAAAAAAAGTTAATTTTATTTTCTTGTTCATTTGAAATAAAAAATATA

AAATTTATAATTAATAATAAATCATAAAAAAAGAAAAACAGATAATATTAAAATTATTTT

TAATAGATAAGAACATTTGAAACAAAAGAAAAGTTTTTCCGGAAAAAATATATGTTTT

TAAAAATAGAGAAGAGAAATCTCTTCTCCAAAGGTTATTTTAAAGCTCTTTTTTTTTTGT

TTTGAAATTTTGTTTGTTAAAAGAAATTATTTTTTAAAAAATTTCTCAAAATATCTATTT

GACTTGATTTTTATTTTTAAGAGACAGATAAGTTGAAAAAAAAAATCAAATTAAATCGGC

ACTAAATGTTGAAAAAATTTAAAATTAATTACTAGAAGAAATATTTATGGGGGAAGAAAT

TTTAATTTCAGAAGAAAATAGAAAAAATTATATGTTTGAGTAGCTAGGCACCTAGCTGT

TTTTAGTAGAGTTGACTTGGGCCACAATGGGAATGTGCTGTCTGACAGTCAAGGACGTGG

CTATCCAACCACACTGTCAATCAAAAACCCACCAATCAGTCTTCCTCCTCCCCCTCCCCA

GCCTCTTTTACAAAGTACATACGTATATTTTCTTTTCTGTATTTTTGTTAGTTATAGTAC

AAATCAAATCGGGTTTTAAGGGAATTTTTAATCTACAAACTATTTCTATACACAAAATTA

GCCATACTAAGGAAGAAAAAAAAATTAATAATATAGCACATTAGTAATATAAAATTAATTA

CTCGATACAATGATAAAATTGCTTCAGTTTTACATCAAAACTTGATTAAAAAAATTATCG
```

-continued

```
ATTGATTTTTCTTTTTAATCTTTAAATTTAATAATTTTTTTCCCTTAAATTTAACACGAT
AAGAATGTTCGAATGAGAGTCGGATGCTAGCTGAAGTTACTAATTAAGAAAAAAGTATAC
AACTTTTTAGCAAAAATGAATAATAGGATATTTGGTTTTATTATCCTATTATTCACTATT
TTGCTAAAAAGTTGTATAATTTTTATAAAAAAAATAAATAAAGGGGAAAAAGAGGATAA
AAAAATACTCAATGCTACCTAATAAAATGGCTACATACGGGTAGACAACAACTCATGCTA
CGAAAATTGCAATTCCATGTTCCCCTGTTGCTAATTTGCGCCATTGCTTTTGCTTACCTG
CCCTTAATTGCTAACCTCTATATAAGCACAAGTCCATATTGCTTTTTGGTCACCGCCACA
TTCCTCACTCTCTCGTCACTCTTTTATTTTTTTTTCTGGTTTCCTTTGTGCGCCAAAAC
TTAAGCTTAAGTAAAAGCAAACAATATGAAATCAACAAACATGAATGGTTCCTCTCCTAA
TGTCTCGGAAGAAACTGGTCGGACCTTAGTCGTTGGTTCGGGTGGGTTTATGGGCCGGTT
CGTCACCGAAGCCAGCCTAGACTCCGGCCGTCCTACGTATATTTTGGCTCGGTCTAGTTC
GAACTCTCCTTCCAAAGCCTCCACCATCAAGTTTCTTCAAGACAGAGGAGCCACTGTTAT
TTACGTATGTACAATTCTCCCTCGACACCTCTTCCATTTTCTGGTTACATTTCCACACGT
ATACAAATACATATACATTTCTAATGTGTAATTATTTGTGTATATTTATATATATGTAAT
GTATAATGTGTAATTATTTATGTATGTATATATGTATGTATGTATGTATGTATGTATATA
TGTATGTACGGACGTTATACAATCTTCGGAATTGTTGTAACAGGGCTCTATCACAGACAA
AGAATTCATGGAGAAGGTTCTGAAAGAACATAAGATAGAAGTTGTAATATCTGCAGTGGG
AGGGGGAAGCATCTTAGACCAGTTCAATCTGATAGAGGCTATCAGGAATGTTGACACTGT
CAAGGTATATGCTCAAAACAACAACTAACATTCATAGGGGAAGAAACTTAGATCTTGTAT
ATGGTCAATGTAGTGACTTGTTTGGTATGTTTGAGCTTCTAGTTAGAATAAAACACTTAT
TGCATGCCTAGCTAAAAGTTAGGAACTTCTTTTGAAAACTAGTTTAGCTAGAGCTAAGCT
ATTCTAAGCAAGAAGACATTAAATAGTACCTAAAGCTATGTTTTTCTATTTAATTCAACA
AGCATTGCACAAAATGGGTTAATGAGTCAAAGGTGAATCTGTTGCAGAGGTTCTTACCGT
CTGAATTCGGGCACGACACAGACAGGGCTGACCCGGTGGAGCCAGGGCTGACCATGTATG
AACAAAAGAGGCAGATTAGGAGGCAGATAGAGAAATCTGGGATTCCTTACACTTACATAT
GTTGCAATTCCATTGCAGCTTGGCCCTACCACGACAACACTCACCCTGCAGATGTTCTGC
CACCCCTAGATAGGTTCAAAATCTACGGTGATGGCACTGTCAAAGGTACCTCATCTTTCT
TTTTTCCTTCATTGGTTTTGTTTTTGTGTATCTTGACTTTAGTGTGGTTGGTAGATGGAA
AACGATAGCATAGAAATTTGGGAAGAGAAGGATGGATGAGAGATTTTGGTTTTCCAAGAA
AATCAATGTCCCAGGATCTCTCATTAAATAACCACCTCCCACATGATATTCCATCTTATC
ATATCAAAGTAAATAGATTACTAGCATTTGTTTGCTTGAGTTTTAAATGTCTTCTATTAG
AAGCTAACATTGGGAAATTAATTAGAGGTCAGATCATAGGAAAAATTTTAATGGTTGAG
GTAAATGTTGCCTGCAATTTAATTCTGACATTGGTTGAGTTTGGTGAAACAAGAAAAATT
TGAGTTAATTAGTGGTTTGTCTCTGTTGTTTACAAAGATAGATAATACTGGATCTCTTAG
TTTGGCTGGCAAATATTCAGCAGTCTTACAGTTTTAAGAACAAATGCTGCCTACCTACTG
CCATCCCATTTTCTAGTAGAAGAAGGAAGAGACAAGGGACTGAATCTTTTGAAATGAAAA
AACCAAAACACATGTAAATGATTGGATAAGAAAAAATATTAGGGAAAAAAAGAAATAGCA
GTCATAGTCAAAGTGCTGATCAGGTGTCTAGATATATACAGGTATAGCATGTTATATTCT
AGACGAAGGCACTGTATGGCAGCAGGTATAGGCTTCAAATAAACTTTTATCTTATATGGC
CTGCTGCTTTGACGAAATTGAAAATTTATCATCAACTAGGCCAATTATCGTTTAATTCAA
```

-continued
```
AATAGCTTTCAAACTAACCTAAATGGCCATTTCTTCAAAGCCCCGAGTAAACCTTTTTGT
CCCATCTTTTTGGTAGTCGATAGTATCCACTTCATTTGGTTAATGCAATTATTTCATTCT
AAACATTTCTGCTTCAATAATGACTTCCTCCAAATCTGGATAGCCAGAAGGGATATTTTC
TACCAAATTGGAAGCTTTGAACTCACAGGCGAAAAGGGGTAATTTTTTTTCTACCATGCC
GTAACCAGCATAATATCATCACAAATCCATGATCATATTTTTACTAAATAGATCTCATAT
TTCATAGTATTTCTTACAGCTCTAAACCTACTCATTCAGCATTGTAAAATTGAGCAGCCA
AGAGAGCTAGTCCAGCTTGTCCTTTTGATAGAGGACAAAGGAGAAAGAGTCTTAGTCAAA
GTACAATGCACCCTGCTTCCTCTTTTTCTTTAGTAAAATAGTAGAAGCGACACCAGTTCT
AAATAGGTTTTGCATCTTGGCTAGTTCCAAGAAATTTGCTAGTCATTAAGGCAATGCCCC
ATTAGGAAGGAAAAGTCGTAAGAATCGGTGGACCTCCCTTAGATTCCCAACGGATAGAAT
GATGTTTTGCTTCTTTCTTCTTGTTGTTGAGCAGCACTGAGAGGCACGTGACTGCTATGA
TGGGTTAGGTAGCAGATTATCACGTGACCCCATCCTCTCCTAACACTTTCCCATCCCTTT
CCTTCTTTTCACCCCCAACAAACACACAAAAAGGGTTATTTATTAGCTACCGGGAACATT
ACATTAAAGCATCAAGTTAATAATAGTTTGGGAATTGAATTTTTAAACCTTTGACTCCGT
CAGTTTAGATCTTTCATTTTCAAATTGAGTTATTAATAAATTATTACAAAATAATTGACA
TAATATAGGACAACCCAATTTACTTGGGTAATCACTATATTTTAAAGGCTATGTTGTTAG
GCAGCCTATTCTAGGAGGAGTCAATGTCGACAACTGGACATTTGGGGTAAAAAGAAGTCC
AAGATTTGATCATTCATAGGCTGTCCTAAGCTAATCGAAAAGGAGGAAGTCCCAACTAAT
TAACTGTTTTGGTAAACAAGTTTATTCTCAAGAGAGGACCACCGAATTCATGTCAGAGAT
TTGCTTATTAATTCAAAGATTTGGACTTTTGGATGTTGCCCGTGAGTTTCTGACGTTGGC
TCAGAGCAAGTCTTTGATCTTCTTGTCAAAGAAACTGCTCTACCCTTCTAATAATGAGTA
AACCAGTCACAGAAAGCAACCCCCAGGTCCAACCTACTCTTCAACAGTTTGCTAGTTTAA
AAAAAGAAAAAGAAAAATTGGGGTTTGCATGTACCTAAGTTACCATCTCTGCATTGAATT
TAAGTTGTAGTAGTAGTTGTAAAATAAAGTCTAGAACCAAAAGCTTTTAATGAAAGACAA
CTTAGGTCCATAACTCACCATCATTATGAGAATTTTGAATATCAATCACCTTACTGTATA
TTATTTATGATGTTGACTCTATGATTTTGTGGTGAATGCCCAGCATACTTTGTGGCGGGT
ACCGATATTGGGAAGTTCACTATAATGTCGATAGAAGATGATCGAACACTGAACAAAACT
GTCCATTTTCAACCTCCAAGCAACCTACTAAACATAAACGAGATGGCCTCACTATGGGAG
GAGAAGATTGGACGTACACTTCCTAGGGTCACCATCACAGAAGAAGATCTGCTGCAGATG
GCCAAAGGTTTGTCCTAATTATTTTCAGTTTTCTTTAAGGTTTTGGTTCAAGCAACTTAA
CCTTTCTCCAAGGAACTATATGCCACTCGGTTGGCTCCATTAAGCATTAATCCATGAAGC
AGTAAGTTCTTGCCTAACAAAATGGATGCTAACCCAACTTCTGATATAAATGCAGAGATG
CGGATCCCACAGAGTGTGGTTGCAGCATTAACTCATGATATTTTCATAAATGGCTGCCAA
ATAAACTTTAGCTTGGACAAGCCAACTGATGTTGAAGTCTGCTCCCTCTACCCAGACACT
CCTTTTCGAACCATCAACGAGTGCTTCGAGGACTTTGCCAAGAAGATAATTGATAATGCC
AAAGCAGTGAGCAAGCCAGCGGCAAGCAACAATGCAATATTTGTGCCAACTGCTAAGCCA
GGAGCATTGCCTATCACTGCGATATGCACATGAGAAATATCTCACTCTATCCATTTCCAC
ATCAATAATTCTTTTACAAGTTCTTTTAATCGTACAATGGTAAGAGACTTATCTGTTGCC
AGTGTTTCCGGCAAAAACTAATCANATGTATCTCTTGAATAAATATC
```

-continued gi|290579512|gb|GU324346.1|Theobroma cacao TT2 like MYB
transcription factor (TcMYBPA) complete cds (SEQ ID NO: 13)

ATGGGAAGGGCTCCTTGTTGTTCTAAAGTTGGGTTGCATAGAGGTCCCTGGACTCCTAGA

GAAGACACATTGCTTGTCAAGTACATTCAAGCTCATGGTGACGGTCACTGGAGATCACTT

CCTAAGAAAGCCGGGCTTCTTAGGTGTGGAAAGAGTTGCAGGCTCAGATGGATGAACTAT

TTAAGACCAGATATAAAGAGAGGGAATATAACTCCCGATGAGGATGATCTTATCATCAGA

TTACATTCCCTCCTCGGCAATCGGTGGTCACTCATTGCCGGAAGGCTTCCTGGTCGAACC

GATAACGAGATTAAAAATTACTGGAACACCCATCTGAGTAAAAGACTTCTAAGCCAAGGG

ACTGACCCTAACACCCACAAGAAACTATCAGAGCCCCCAGTTCAACAAGTGAAGAAGAGA

AAAAGCAGCAGAGGCAACAGCAACAAGAAGCAGAACAATAGCAAGGGCAAAGGCGCAAAG

GTTGAGCCAGAAGAGCCCAAAGTCCATCTCCCTAAGCCCGTTAGAGTAACTTCTTTCTCT

TTACCAAGAAACGACAGCTTTGACCAATGTAATACGTTTAGCACGGTGTCTTCAAGCCAA

GGAGGAGAGGGAGGATTGGGTACAGAGGTTGTACAGGGACCTTGGTCAGATAATGTCAAC

GATGATGAAAATGGGACCGGATTTCTTGCTGCTTATGATGATCATGGTTTTGTTAACGGT

TCAGATTTCGAGTGCCAGTCTCATGTACCAGCAAGTGATGACGATAATTCTCTCGAGAAG

CTTTACGAAGAGTATCTCCAGCTTCTGAAGACAAACGATGATCAAGTGCAGTTGGATTCT

TTCGCTGAATCATTATTGATCTGA

ADD51352.1 GI:290579513 Theobroma cacao TT2 like MYB
transcription factor (TcMYBPA) amino acid sequence.

(SEQ ID NO: 14)

```
  1   mgrapccskv glhrgpwtpr edtllvkyiq ahgdghwrsl pkkagllrcg kscrlrwmny 61   lrpdikrgni tpdeddliir lhsllgnrws liagrlpgrt dneiknywnt hlskrllsqg 121   tdpnthkkls eppvqqvkkr kssrgnsnkk qnnskgkgak vepeepkvhl pkpvrvtsfs 181   lprndsfdqc ntfstvsssq ggegglgtev vqgpwsdnvn ddengtgfla ayddhgfvng 241   sdfecqshvp asdddnslek lyeeylqllk tnddqvqlds faeslli
```

The invention features methods and materials related to modulating (e.g., increasing or decreasing) flavonoid levels in caco plants. The methods can include transforming a *cacao* plant cell with a nucleic acid encoding a flavonoid-modulating polypeptide, wherein expression of the polypeptide results in a modulated level of one or more flavonoids. *Cacao* plant cells produced using such methods can be grown to produce plants having an increased or decreased flavonoid content. Such plants may be used to produce, for example, foodstuffs having an increased nutritional content, and/or modified appearance or color, which may benefit both food producers and consumers, or can be used as sources from which to extract one or more flavonoids.

Polypeptides

The term "polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

Polypeptides described herein include flavonoid-modulating polypeptides. Flavonoid-modulating polypeptides can be effective to modulate flavonoid levels when expressed in a plant or plant cell. Modulation of the level of flavonoid can be either an increase or a decrease in the level of flavonoid relative to the corresponding level in a control plant.

A flavonoid-modulating polypeptide can be an enzyme in the flavonoid biosynthetic pathway, for example, any of the enzymes listed in FIG. 1. More specifically, useful flavonoid modulating polypeptides include those involved in the biosynthesis of proanthocyanidins and anthocyanins as shown in FIG. 2. Flavonoid-modulating polypeptides include for example, anthocyanidin reductase, anthrocyanidin synthase, and leucocyanidin reductase. SEQ ID NOs.: 2 and 3 set forth amino acid sequences of predicted *T. cacao* anthocyanidin reductases. SEQ ID NOs: 6 and 7 set forth amino acid sequences of predicted *T. cacao* anthocyanidin synthases. SEQ ID NOs: 10 and 11 set forth amino acid sequences of predicted *T. cacao* leucanthocyanidin reductases.

A flavonoid-modulating polypeptide can also be a polypeptide that regulates the synthesis of a flavonoid biosynthetic enzyme, for example, a transcription factor. Transcription factors are a diverse class of proteins that regulate gene expression through specific DNA binding events. Transcription factors are involved in a variety of regulatory networks of genes in plants, including those genes responsible for the biosynthesis of metabolites. Transcription factors include a number of characteristic structural motifs that mediate interactions with nucleic acids. An exemplary transcription factor is a TT2-like MYB transcription factor (TcMYBPA). SEQ ID NOs.: 14 sets forth an amino acid sequence of predicted *T. cacao* TT2-like MYB transcription factor (TcMYBPA).

A flavonoid-modulating polypeptide can comprise any of the amino acid sequences set forth in SEQ ID NOs: 2, 3, 6, 7, 10, 11 or 14. Alternatively, a flavonoid-modulating polypeptide can be a homolog, ortholog, or variant of the polypeptide having an amino acid sequence set forth in SEQ ID NOs: 2, 3, 6, 7, 10, 11 or 14. For example, a flavonoid-modulating polypeptide can have an amino acid sequence with at least 45% sequence identity, e.g., 45%, 50%, 55%, 60%, 65%, 70%, 75%, 80%, 85%, 90%, 95%, 97%, 98%, or 99% sequence identity, to an amino acid sequence set forth in SEQ ID NOs: 2, 3, 6, 7, 10, 11 or 14.

A flavonoid-modulating polypeptide encoded by a recombinant nucleic acid can be a native flavonoid-modulating polypeptide, i.e., one or more additional copies of the coding sequence for a flavonoid-modulating polypeptide that is naturally present in the cell. Alternatively, a flavonoid-modulating polypeptide can be heterologous to the cell, e.g., a transgenic *T. cacao* plant can contain the coding sequence for a flavonoid-modulating polypeptide from another plant species.

A flavonoid-modulating polypeptide can include additional amino acids that are not involved in flavonoid modulation, and thus can be longer than would otherwise be the case. For example, a flavonoid-modulating polypeptide can include an amino acid sequence that functions as a reporter. Such a flavonoid-modulating polypeptide can be a fusion protein in which a green fluorescent protein (GFP) polypeptide is fused to, e.g., SEQ ID NOs: 2, 3, 6, 7, 10, 11 or 14, or in which a yellow fluorescent protein (YFP) polypeptide is fused to, e.g., SEQ ID NOs: 2, 3, 6, 7, 10, 11 or 14. In some embodiments, a flavonoid-modulating polypeptide includes a purification tag, a chloroplast transit peptide, a mitochondrial transit peptide, an amyloplast transit peptide or a leader sequence added to the amino or carboxy terminus.

Flavonoid-modulating polypeptides suitable for use in the invention can be identified by analysis of nucleotide and polypeptide sequence alignments. For example, performing a query on a database of nucleotide or polypeptide sequences can identify homologs and/or orthologs of flavonoid-modulating polypeptides. Sequence analysis can involve BLAST, Reciprocal BLAST, or PSI-BLAST analysis of nonredundant databases using known flavonoid-modulating polypeptide amino acid sequences. Those polypeptides in the database that have greater than 40% sequence identity can be identified as candidates for further evaluation for suitability as a flavonoid-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains suspected of being present in flavonoid-modulating polypeptides, e.g., conserved functional domains.

The identification of conserved regions in a template or subject polypeptide can facilitate production of variants of wild type flavonoid-modulating polypeptides. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains at sanger.ac.uk/Pfam and genome.wustl.edu/Pfam. A description of the information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999).

Conserved regions also can be determined by aligning sequences of the same or related polypeptides from closely related species. Closely related species preferably are from the same family. In some embodiments, alignment of sequences from two different species is adequate. For example, sequences from *Arabidopsis* and *Zea mays* can be used to identify one or more conserved regions.

Typically, polypeptides that exhibit at least about 40% amino acid sequence identity are useful to identify conserved regions. Conserved regions of related polypeptides can exhibit at least 45% amino acid sequence identity (e.g., at least 50%, at least 60%, at least 70%, at least 80%, or at least 90% amino acid sequence identity). In some embodiments, a conserved region of target and template polypeptides exhibit at least 92%, 94%, 96%, 98%, or 99% amino acid sequence identity. Amino acid sequence identity can be deduced from amino acid or nucleotide sequences. In certain cases, highly conserved domains have been identified within flavonoid-modulating polypeptides. These conserved regions can be useful in identifying functionally similar (orthologous) flavonoid-modulating polypeptides.

In some instances, suitable flavonoid-modulating polypeptides can be synthesized on the basis of consensus functional domains and/or conserved regions in polypeptides that are homologous flavonoid-modulating polypeptides. Domains are groups of substantially contiguous amino acids in a polypeptide that can be used to characterize protein families and/or parts of proteins. Such domains have a "fingerprint" or "signature" that can comprise conserved (1) primary sequence, (2) secondary structure, and/or (3) three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Useful polypeptides can be constructed based on the conserved regions in SEQ ID NOs: 2, 3, 6, 7, 10, 11 or 14. Such a polypeptide includes the conserved regions arranged in the order depicted in a Figure from amino-terminal end to carboxy-terminal end and has at least 80% sequence identity to an amino acid sequence corresponding to any one of SEQ ID NOs: 2, 3, 6, 7, 10, 11 or 14.

Nucleic Acids

The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An "isolated" nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

As used herein, the term "percent sequence identity" refers to the degree of identity between any given query sequence and a subject sequence. A subject sequence typically has a length that is more than 80 percent, e.g., more than 82, 85, 87, 89, 90, 93, 95, 97, 99, 100, 105, 110, 115, or 120 percent, of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chema et al., Nucleic Acids Res., 31(13):3497-500 (2003).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tm-c.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Recombinant constructs can be used to transform plants or plant cells in order to modulate flavonoid levels. A recombinant nucleic acid construct can comprise a nucleic acid encoding a flavonoid-modulating polypeptide as described herein, operably linked to a regulatory region suitable for expressing the flavonoid-modulating polypeptide in the plant or cell. Thus, a nucleic acid can comprise a coding sequence that encodes any of the flavonoid-modulating polypeptides as set forth in SEQ ID NOs: 2, 3, 6, 7, 10, 11 or 14.

In some cases, a recombinant nucleic acid construct can include a nucleic acid comprising less than the full-length coding sequence of a flavonoid-modulating polypeptide. For example, a recombinant nucleic acid construct can comprise a flavonoid-modulating nucleic acid having the nucleotide sequence set forth in SEQ ID NO: 1, 5, 9 or 13. In some cases, a recombinant nucleic acid construct can include a nucleic acid comprising a coding sequence, a gene, or a fragment of a coding sequence or gene in an antisense orientation so that the antisense strand of RNA is transcribed.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given flavonoid-modulating polypeptide can be modified such that optimal expression in a particular plant species is obtained, using appropriate codon bias tables for that species.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag® tag (Kodak, New Haven, Conn.) sequences typically are expressed as a fusion with the encoded polypeptide. Such tags can be inserted anywhere within the polypeptide, including at either the carboxyl or amino terminus.

Regulatory Regions

The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., The Plant Cell, 1:977-984 (1989). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano et al., Plant Cell, 1:855-866 (1989); Bustos et al., Plant Cell, 1:839-854 (1989); Green et al., EMBO J., 7:4035-4044 (1988); Meier et al., Plant Cell, 3:309-316 (1991); and Zhang et al., Plant Physiology, 110:1069-1079 (1996).

Examples of various classes of promoters are described below. It will be appreciated that a promoter may meet criteria for one classification based on its activity in one plant species, and yet meet criteria for a different classification based on its activity in another plant species.

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root-active promoters confer transcription in root tissue, e.g., root endodermis, root epidermis, or root vascular tissues. In some embodiments, root-active promoters are root-preferential promoters, i.e., confer transcription only or predominantly in root tissue. Examples of root-preferential promoters include the root-specific subdomains of the CaMV 35S promoter (Lam et al., Proc. Natl. Acad. Sci. USA, 86:7890-7894 (1989)), root cell specific promoters reported by Conkling et al., Plant Physiol., 93:1203-1211 (1990), and the tobacco RD2 promoter.

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the vicilin promoter, the napin promoter, the Arcelin-5 promoter, the phaseolin promoter (Bustos et al., Plant Cell, 1(9):839-853 (1989)), the soybean trypsin inhibitor promoter (Riggs et al., Plant Cell, 1(6):609-621 (1989)), the ACP promoter (Baerson et al., Plant Mol. Biol., 22(2): 255-267 (1993)), the stearoyl-ACP desaturase promoter (Slocombe et al., Plant Physiol., 104(4):167-176 (1994)), the soybean a' subunit of .beta.-conglycinin promoter (Chen et al., Proc. Natl. Acad. Sci. USA, 83:8560-8564 (1986)), the oleosin promoter (Hong et al., Plant Mol. Biol., 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., Mol. Cell. Biol., 13:5829-5842 (1993)), the beta-amylase promoter, and the barley hordein promoter.

Promoters that are active in ovary tissues such as the ovule wall and mesocarp can also be useful, e.g., a polygalacturonidase promoter, the banana TRX promoter, and the melon actin promoter. To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters. Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (Plant Cell Rep (2001) 20:647-654).

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., Plant Cell Physiol., 35:773-778 (1994)), the Cab-1 promoter from wheat (Fejes et al., Plant Mol. Biol., 15:921-932 (1990)), the CAB-1 promoter from spinach (Lubberstedt et al., Plant Physiol., 104:997-1006 (1994)), the cab1R promoter from rice (Luan et al., Plant Cell, 4:971-981 (1992)), the pyruvate orthophosphate dikinase (PPDK) promoter from corn (Matsuoka et al., Proc. Natl. Acad. Sci. USA, 90:9586-9590 (1993)), the tobacco Lhcb1*2 promoter (Cerdan et al., Plant Mol. Biol., 33:245-255 (1997)), the *Arabidopsis thaliana* SUC2 sucrose-H+ symporter promoter (Truernit et al., Planta, 196:564-570 (1995)), and thylakoid membrane protein promoters from spinach (psaD, psaF, psaE, PC, FNR, atpC, atpD, cab, rbcS).

Examples of promoters that have high or preferential activity in vascular bundles include the glycine-rich cell wall protein GRP 1.8 promoter (Keller and Baumgartner, Plant Cell, 3(10):1051-1061 (1991)), the *Commelina* yellow mottle virus (CoYMV) promoter (Medberry et al., Plant Cell, 4(2):185-192 (1992)), and the rice tungro bacilliform virus (RTBV) promoter (Dai et al., Proc. Natl. Acad. Sci. USA, 101(2):687-692 (2004)).

Promoters having preferential activity in sieve, laticifer, and/or companion cells are also considered vascular tissue promoters.

Inducible promoters confer transcription in response to external stimuli such as chemical agents or environmental stimuli. For example, inducible promoters can confer transcription in response to hormones such as gibberellic acid or ethylene, or in response to light or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site. Other classes of promoters include, but are not limited to, leaf-preferential, stem/shoot-preferential, callus-preferential, guard cell-preferential, tuber-preferential, parenchyma cell-preferential, and senescence-preferential promoters.

Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, more than one regulatory region can be operably linked to the sequence of a polynucleotide encoding a flavonoid-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Transgenic Plants and Plant Cells

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant. Progeny includes descendants of a particular plant or plant line. Progeny of an instant plant include seeds formed on $F_1$, $F_2$, F3, F4, F5, F6 and subsequent generation plants, or seeds formed on $BC_1$, $BC_2$, $BC_3$, and subsequent generation plants, or seeds formed on $F_1BC_1$, $F_3BC_2$, $F_1BC_3$, and subsequent generation plants. The designation F1 refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous flavonoid-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

Transgenic Plant Phenotypes

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known.

A population of transgenic plants can be screened and/or selected for those members of the population that have a desired trait or phenotype conferred by expression of the transgene. For example, a population of progeny of a single transformation event can be screened for those plants having a desired level of expression of a flavonoid-modulating polypeptide or nucleic acid. As an alternative, a population of plants comprising independent transformation events can be screened for those plants having a desired level of a flavonoid. Selection and/or screening can be carried out over one or more generations, which can be useful to identify those plants that have a desired trait, such as increased amounts of one or more flavonoids. Selection and/or screening can also be carried out in more than one geographic location. In some cases, transgenic plants can be grown and selected under conditions which induce a desired phenotype or are otherwise necessary to produce a desired phenotype in a transgenic plant. In addition, selection and/or screening can be carried out during a particular developmental stage in which the phenotype is exhibited by the plant.

Transgenic plants can have an altered phenotype as compared to a corresponding control plant that either lacks the transgene or does not express the transgene. A polypeptide can affect the phenotype of a plant (e.g., a transgenic plant) when expressed in the plant, e.g., at the appropriate time(s), in the appropriate tissue(s), or at the appropriate expression levels. Phenotypic effects can be evaluated relative to a control plant that does not express the exogenous polynucleotide of interest, such as a corresponding wild type plant, a corresponding plant that is not transgenic for the exogenous polynucleotide of interest but otherwise is of the same genetic background as the transgenic plant of interest, or a corresponding plant of the same genetic background in which expression of the polypeptide is suppressed, inhibited, or not induced (e.g., where expression is under the control of an inducible promoter). A plant can be said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

Thus, a transgenic plant or cell in which the expression of a flavonoid-modulating polypeptide is modulated can have modulated levels of one or more flavonoids relative to the flavonoid levels in a control plant that lacks or does not express the transgene. An amount of one or more of any individual flavonoid compounds can be modulated, e.g., increased or decreased, relative to a control plant not transgenic for the particular flavonoid-modulating polypeptide using the methods described herein. In certain cases, therefore, more than one flavonoid compound (e.g., two, three, four, five, six, seven, eight, nine, ten or even more flavonoid compounds) can have its amount modulated relative to a control plant or cell that is not transgenic for a flavonoid-modulating polypeptide described herein.

In some embodiments, a plant in which expression of a flavonoid-modulating polypeptide is modulated can have increased levels of one or more flavonoids in one or more tissues, e.g., aerial tissues, fruit tissues, root or tuber tissues, leaf tissues, stem tissues, or seeds. The increase in amount of one or more flavonoids can be restricted in some embodiments to particular tissues and/or organs, relative to other tissues and/or organs. For example, a transgenic plant can have an increased amount of a flavonoid in fruit tissue relative to leaf or root tissue.

The amount of one or more flavonoid compounds can be increased or decreased in a transgenic plant expressing a flavonoid-modulating polypeptide as described herein. An increase can be from about 2% to about 400% on a weight basis (e.g., a fresh or freeze dried weight basis) in such a transgenic plant compared to a corresponding control plant that lacks the recombinant nucleic acid encoding the flavonoid-modulating polypeptide. The flavonoid levels can be increased by at least 2 percent, e.g., 2, 5, 10, 15, 20, 25, 30, 35, 40, 45, 50, 55, 60, 65, 70, 75, 80, 85, 90 or more than 90 percent, as compared to the flavonoid levels in a corresponding control plant that does not express the transgene. In some embodiments, the increase is from about 5% to about 50%, or about 10% to about 40%, or about 50% to about 75%, or about 100% to about 200%, or about 200% to about 500% higher than the amount in a corresponding control cell that lacks the recombinant nucleic acid encoding a flavonoid-modulating polypeptide. In some embodiments, an increase can be from about 1.2-fold to about 10-fold, or about 1.2-fold to about 8-fold, or about 1.2-fold to about 6-fold, or about 1.2-fold to about 5-fold, or about 1.2-fold to about 4-fold, or about 1.2-fold to about 3-fold, or about 1.2-fold to about 2-fold, or about 1.3-fold to about 6-fold, or about 1.3-fold to about 5-fold, or about 1.3-fold to about 4-fold, or about 1.3-fold to about 3-fold, or about 1.3-fold to about 2.5-fold, or about 1.3-fold to about 2-fold, or about 1.3-fold to about 1.5-fold, or about 1.5-fold to about 6-fold, or about 1.5-fold to about 5-fold, or about 1.5-fold to about 4-fold, or about 1.5-fold to about 3-fold, or about 1.5-fold to about 2-fold, or about 2-fold to about 6-fold, or about 3-fold to about 4-fold, or about 3-fold to about 7-fold, or about 4-fold to about 8-fold, or about 5-fold to about 10-fold, higher than the amount in corresponding control cells or tissues that lack the recombinant nucleic acid encoding the flavonoid-modulating polypeptide.

In other embodiments, the flavonoid compound that is increased in transgenic plants or plant cells expressing a flavonoid-modulating polypeptide as described herein is either not produced or is not detectable in a corresponding control plant or plant cell that lacks the recombinant nucleic acid encoding the flavonoid-modulating polypeptide. Thus, in such embodiments, the increase in such a flavonoid compound is infinitely higher in a transgenic plant containing a recombinant nucleic acid encoding a flavonoid-modulating polypeptide than in a corresponding control plant or plant cell that lacks the recombinant nucleic acid encoding the flavonoid-modulating polypeptide. For example, in certain cases, a flavonoid-modulating polypeptide described herein may activate a biosynthetic pathway in a plant that is not normally activated or operational in a control plant, and one or more new flavonoids that were not previously produced in that plant species can be produced.

In some embodiments, a plant in which expression of a flavonoid-modulating polypeptide is modulated can have decreased levels of one or more flavonoids in one or more tissues, e.g., aerial tissues, fruit tissues, root or tuber tissues, leaf tissues, stem tissues, or seeds. The decrease in amount of one or more flavonoids can be restricted in some embodiments to particular tissues and/or organs, relative to other tissues and/or organs. For example, a transgenic plant can have a decreased amount of a flavonoid in fruit tissue relative to leaf or root tissue.

The amount of one or more flavonoid compounds can be increased or decreased in a transgenic plant expressing a flavonoid-modulating polypeptide as described herein. A decrease can be from about 2% to about 80% on a weight basis (e.g., a fresh or freeze dried weight basis) in such a transgenic plant compared to a corresponding control plant that lacks the recombinant nucleic acid encoding the flavonoid-modulating polypeptide.

The flavonoid levels can be decreased by at least 2 percent, e.g., 2, 5, 10, 15, 20, 25, 30, 35, 40, 45, 50, 55, 60, 65, 70, 75, 80, or more than 80 percent, as compared to the flavonoid levels in a corresponding control plant that does not express the transgene. In some embodiments, the decrease is from about 5% to about 50%, or about 10% to about 40%, or about 50% to about 75%, or about 60% to about 80% lower than the amount in a corresponding control cell that lacks the recombinant nucleic acid encoding a flavonoid-modulating polypeptide. In some embodiments, the flavonoid level is from about 0.2-fold to about 0.9-fold, or from about 0.3-fold to about 0.8-fold, or from about 0.5-fold to about 0.9-fold or from about 0.4-fold to about 0.9 fold, or from about 0.4-fold to about 0.7-fold lower than the amount in a corresponding control cell that lacks the recombinant nucleic acid encoding a flavonoid-modulating polypeptide.

In certain embodiments, a flavonoid compound that is decreased in transgenic plants or plant cells expressing a flavonoid-modulating polypeptide as described herein is decreased to an undetectable level as compared to the level in a corresponding control plant or plant cell that lacks the recombinant nucleic acid encoding the flavonoid-modulating polypeptide.

In some embodiments, the amounts of two or more flavonoids are increased and/or decreased, e.g., the amounts of two, three, four, five, six, seven, eight, nine, ten (or more) flavonoid compounds are independently increased and/or decreased.

The amount of a flavonoid compound can be determined by known techniques, e.g., by extraction of flavonoid compounds from plants or plant tissues followed by gas chromatography-mass spectrometry (GC-MS) or liquid chromatography-mass spectrometry (LC-MS). If desired, the structure of the flavonoid compound can be confirmed by GC-MS, LC-MS, nuclear magnetic resonance and/or other known techniques.

Typically, a difference (e.g., an increase) in the amount of any individual flavonoid compound in a transgenic plant or cell relative to a control plant or cell is considered statistically significant at $p<0.05$ with an appropriate parametric or non-parametric statistic, e.g., Chi-square test, Student's t-test, Mann-Whitney test, or F-test. In some embodiments, a difference in the amount of any individual flavonoid compound is statistically significant at $p<0.01$, $p<0.005$, or $p<0.001$. A statistically significant difference in, for example, the amount of any individual flavonoid compound in a transgenic plant compared to the amount in cells of a control plant indicates that (1) the recombinant nucleic acid present in the transgenic plant results in altered levels of one or more flavonoid compounds and/or (2) the recombinant nucleic acid warrants further study as a candidate for altering the amount of a flavonoid compound in a plant.

Increases in flavonoids in plants can provide increased yields of flavonoids extracted from the plant tissues and increased nutritional content in foodstuffs and animal feed produced from the plant tissues. Decreases in flavonoids in plants can be useful in situations where altering the color or appearance of a plant is desired.

Information that the polypeptides disclosed herein can modulate flavonoid content can be useful in breeding of crop plants. Based on the effect of disclosed polypeptides on flavonoid content, one can search for and identify polymorphisms linked to genetic loci for such polypeptides. Polymorphisms that can be identified include simple sequence repeats (SSRs), rapid amplification of polymorphic DNA (RAPDs), amplified fragment length polymorphisms (AFLPs) and restriction fragment length polymorphisms (RFLPs).

If a polymorphism is identified, its presence and frequency in populations is analyzed to determine if it is statistically significantly correlated to an alteration in flavonoid content. Those polymorphisms that are correlated with an alteration in flavonoid content can be incorporated into a marker assisted breeding program to facilitate the development of lines that have a desired alteration in flavonoid content. Typically, a polymorphism identified in such a manner is used with polymorphisms at other loci that are also correlated with a desired alteration in flavonoid content.

Methods of Producing Flavonoids

Also provided herein are methods for producing one or more flavonoids. Exemplary flavonoids include, without limitation, dihydroflavonols, flavonols, anthocyanins, isoflavonoids. flavan-4-ols, 3-deoxyanthocyanidins, leucoanthocyanidins, 3-OH-anthocyanins, flavan-3-ols, catechin, epicatechin, (epi)gallocatechin and proanthocyanidins. Such methods can include growing a plant cell that includes a nucleic acid encoding a flavonoid-modulating polypeptide as described herein, under conditions effective for the expression of the flavonoid-modulating polypeptide. Also provided herein are methods for modulating (e.g., altering, increasing, or decreasing) the amounts of one or more flavonoids in a plant cell. The methods can include growing a plant cell as described above, i.e., a plant cell that includes a nucleic acid encoding a flavonoid-modulating polypeptide as described herein. The one or more flavonoids produced by these methods can be novel flavonoids, e.g., not normally produced in a wild-type plant cell.

The methods can further include the step of recovering one or more flavonoids from the cells. For example, plant cells known or suspected of producing one or more flavonoids can be subjected to fractionation to recover a desired flavonoid. Typically, fractionation is guided by in vitro assay of fractions. In some instances, cells containing one or more flavonoid compounds can be separated from cells not containing, or containing lower amounts of the flavonoid, in order to enrich for cells or cell types that contain the desired compound(s). A number of methods for separating particular cell types or tissues are known to those having ordinary skill in the art.

Fractionation can be carried out by techniques known in the art. For example, plant tissues or organs can be extracted with 100% MeOH to give a crude oil which is partitioned between several solvents in a conventional manner. As an alternative, fractionation can be carried out on silica gel columns using methylene chloride and ethyl acetate/hexane solvents.

In some embodiments, a fractionated or unfractionated plant tissue or organ is subjected to mass spectrometry in order to identify and/or confirm the presence of a desired flavonoid(s). In some embodiments, electrospray ionization (ESI) mass spectrometry can be used. In other embodiments, atmospheric pressure chemical ionization (APCI) mass spectrometry is used. If it is desired to identify higher molecular weight molecules in an extract, matrix-assisted laser desorption/ionization time-of-flight (MALDI-TOF) mass spectrometry can be useful.

Articles of Manufacture

Transgenic *cacao* plants provided herein have particular uses in the agricultural and nutritional industries. For example, transgenic plants described herein can be used to make food products. Transgenic plants described herein can also be used to make processed food products such as confections, cereals, beverages, dairy products, e.g., yoghurt, ice creams, ice milks, puddings, energy bars, cookies, breads, desserts, and nutritional supplements. Such products are useful to provide increased amounts of flavonoids in a human diet. Transgenic plants described herein can also be used as a source of animal feeds.

Transgenic plants or tissues from transgenic plants described herein can also be used as a source from which to extract flavonoids, using techniques known in the art. The resulting extract can be included in nutritional supplements and pharmaceuticals. The extracted flavonoids can also be used as starting materials for making fragrance chemicals for perfumes and other cosmetics.

Seeds of transgenic plants described herein can be conditioned and bagged in packaging material by means known in the art to form an article of manufacture. Packaging material such as paper and cloth are well known in the art.

A package of seed can have a label e.g., a tag or label secured to the packaging material, a label printed on the packaging material, or a label inserted within the package. The package label may indicate that the seed herein incorporates transgenes that provide increased amounts of one or more flavonoids in one or more tissues of plants grown from such seeds.

Discovery of Unique Individuals of Porcelana with Enhanced Proanthocyanidin Profiles We have collected seeds from individual plants, fermented them in isolation, and then extracted and measured the molecular composition of proanthocyanidin and flavonoid content of each sample. We have screened a large collection of porcelana plants on our private farms. From this analysis we have identified unique individuals with enhanced PA content.

Discovery of Molecular Markers

Strategies and Approaches

We have observed that there is a natural variation in the expression of flavonoid metabolites in different individuals/genotypes of *cacao* and have identified specific porcelana type *cacao* with unique flavonoid profiles. This natural variation results from differences in the genetic makeup of the plants and may involve changes in promoter structures, enzyme sequence changes, transcription factor changes, or other cellular changes that interact with the flavonoid biosynthetic machinery. These changes result from natural mutations and are generally stable and inheritable changes. By screening a collection of natural variants, and performing molecular analysis, it is possible to identify the genetic basis of these variations, which will reside in a change in the nucleic acid sequences of the genes for flavonoid biosynthesis. The molecular analysis performed includes Quantitative Trait Loci mapping, transcriptome sequencing, genome sequencing or other approaches, which allow the scientists to narrow down then identify candidate mutations. The search is greatly simplified by our knowledge of the entire pathway and the genes for flavonoid biosynthesis and the transcription factors that regulate these structural genes, are the focus of the screens.

The mutations can be absolutely verified as the functional basis of the natural variation by reverse genetics approaches, which include introducing the various alleles of a gene into a transgenic plant and observing the phenotype of the plant to see if there is a functional connection between the gene and the trait. This approach is known as gene discovery and functional genomics. A second validation approach is functional complementation, in which a functionally dominant version of a gene is introduced into a plant not containing the dominant allele, then determining the functional effect of the new gene in the transgenic plant. For example, if one plant has a low expression of a gene and a different plant has a higher expression level, the high expression version of the gene can be moved into the plant containing the lower expressing level, and the resulting transgenic plant examined. If this plant exhibits high gene expression level, then it can be absolutely concluded that the DNA sequence from the high expressing plant is the genetic determinant of this dominant trait.

Once identified, the DNA sequence can be easily converted into molecular marker tools (PCR primers of 17-24 nucleotides in length) SNP markers, or other forms of DNA detection markers, that can be used to distinguish between different versions (alleles) of the genes. The markers can be synthesized as synthetic oligonucleotides.

Use of Molecular Markers

The molecular markers will be used to carry out molecular assisted selection in a breeding program (MAS). Plants carrying different favorable alleles of different genes are crossed by pollination. Progeny of said cross are grown for several weeks and small leaf samples are collected from which DNA is purified. Molecular markers will be applied to test the DNA samples to identify individuals containing favorable alleles of each parent, thus rapidly identifying plants with two or more favorable alleles. This accelerates the breeding progress tremendously by eliminating the need to grow plants to maturity and test for metabolite production.

Analysis

Allele expression can easily be verified by using methods well known in the field including PCR analysis, RTPCR amplification of cDNA from plants to test transcription level of alleles. Western blot analysis of protein extracts from plants to test protein expression level. Enzyme assays of protein extracts from plants to measure specific activity levels. Metabolic analysis of extracts to quantify specific metabolites such as catechin and epicatechin using HPLC and gas chromatographic methods. All these methods are commonly used in the art. The invention encompasses the molecular markers and the plants derived from breeding programs utilizing them.

The studies described in the examples below illustrate the compositions and methods of the invention without limitation.

EXAMPLES

Figure 4:
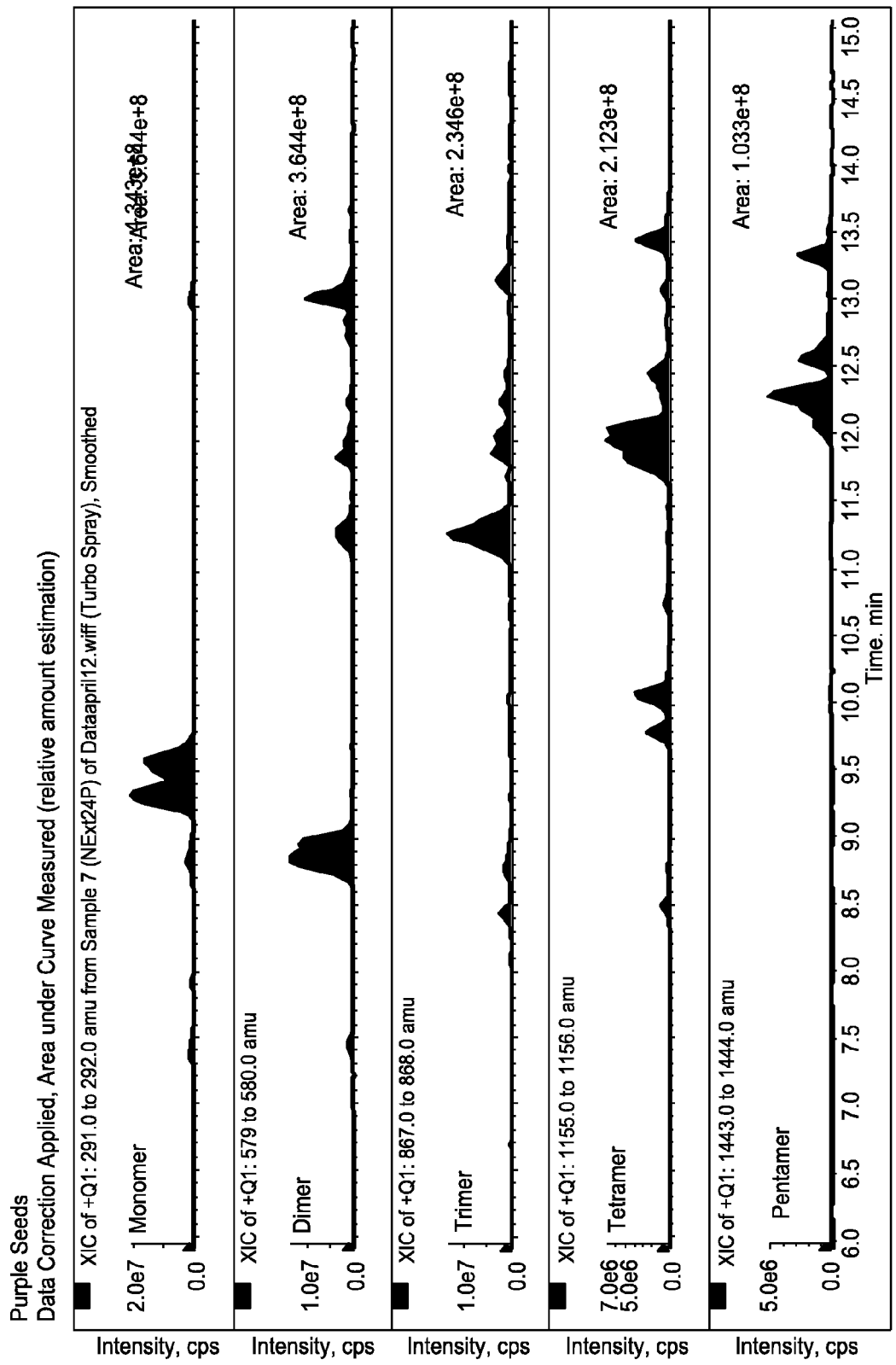
FIG. 4 shows the results of an analysis of proanthocyanidins in purple seeds.

Example 1: Analysis of Proanthocyanidin Content of White and Purple *T. cacao* Seeds The proanthycynanidin (PA) content of white and purple *T. cacao* seeds was analyzed by liquid chromatography. White seed is genotype DR24. Purple seed is also from genotype 24. The seed were taken from a single pod in which genetic segregation resulted in about half white and half purple seeds. The results of this analysis of PAs for the white seeds and the purple seeds are shown in FIGS. 3 and 4, respectively. As shown in FIGS. 3 and 4, the white seeds had higher levels of low molecular weight PAs than did the purple seeds.

Figure 6:
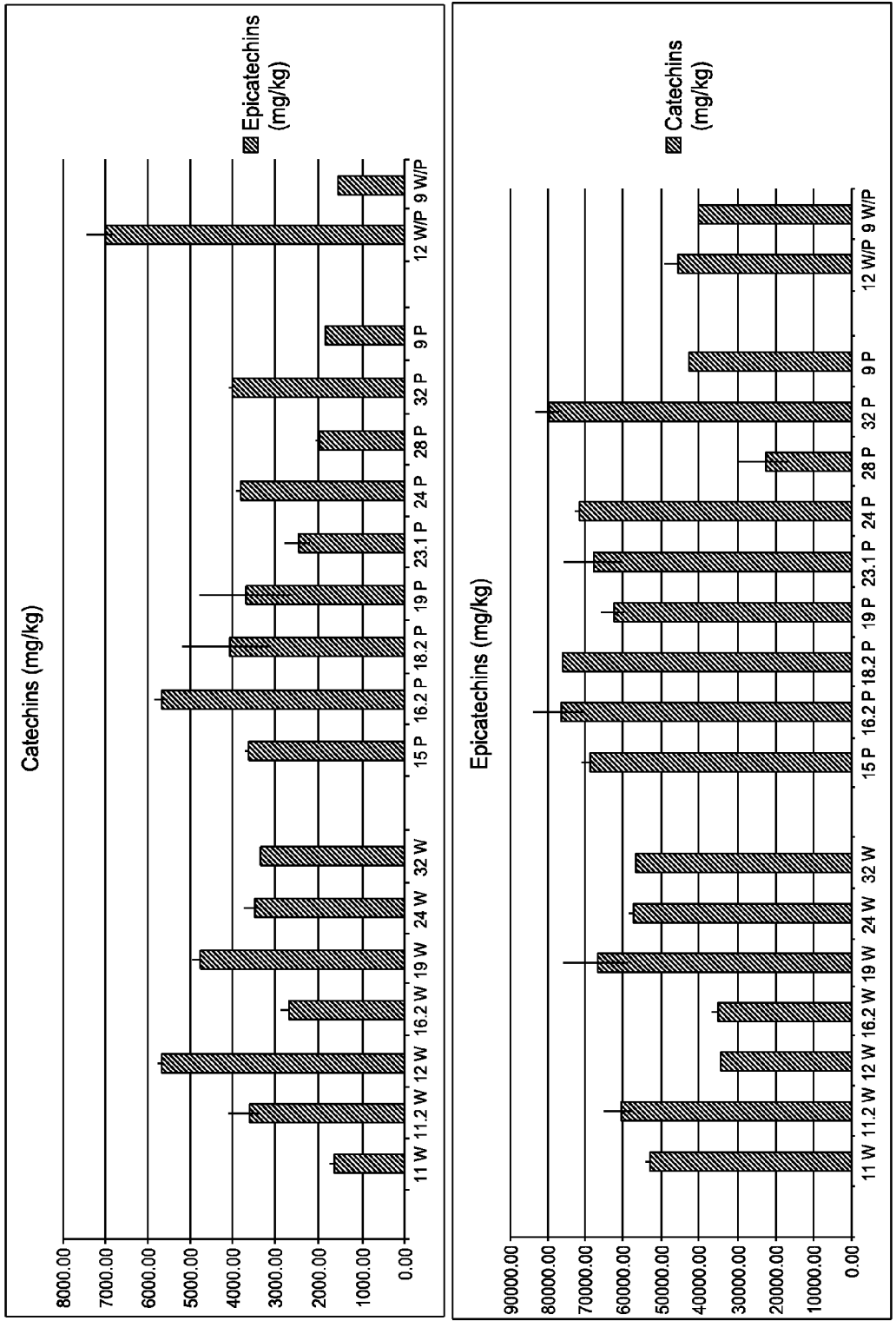
FIG. 6 is a graph depicting the results of an analysis of levels of catechins and epicatechins in 15 different varieties of *cacao*.

Example 2: Analysis of Levels of Catechins and Epicatechins in Seeds from Different *T. cacao* Genotypes Levels of catechins and epicatechins in were analyzed by LCMS in extracts from seeds of 15 different varieties of *T. cacao* from the Dominican Republic. Mean catechin and epicatechin levels were determined relative to known standards. Standard deviations were calculated from two replications. The results of this analysis are shown in the table in FIG. 5 and depicted graphically in FIG. 6.

W=white seeds, P=purple seeds, W/P=light purple seeds. The numbers indicate individual trees tagged in the field in the Dominican Republic. As shown in FIGS. 3 and 4, different *T. cacao* varieties accumulated differing levels of catechins and epicatechins.

What is claimed is:

1. A method of modulating the levels of a flavonoid in a cacao plant, the method comprising introducing into a cacao plant cell an exogenous nucleic acid comprising a regulatory region operably linked to a nucleic acid sequence encoding a flavonoid-modulating polypeptide, wherein the flavonoid-modulating polypeptide comprises an amino acid sequence having 95% or greater sequence identity to an amino acid sequence selected from the group consisting of SEQ ID NO:10 and SEQ ID NO:11, wherein a plant produced from the plant cell has a different flavonoid level compared to the corresponding level in a corresponding control plant that does not comprise the nucleic acid.

2. The method of claim 1, wherein the sequence identity is 99% or greater.

3. The method of claim 1, wherein the modulation is an increase.

4. The method of claim 1, wherein the modulation is a decrease.

5. The method of claim 1, wherein the flavonoid is a proanthocyanidin or an anthocyanidin.

6. The method of claim 1, wherein the regulatory region is a promoter.

7. The method of claim 6, wherein the promoter is a cell-specific or tissue specific promoter.

8. The method of claim 7, wherein the tissue specific promoter is a seed-specific promoter.

9. The method of claim 8, wherein the seed-specific promoter is a vicilin promoter.

10. A method of producing a cacao plant having a modulated level of one or more flavonoids, the method comprising:
(a) introducing into a plurality of plant cells an isolated nucleic acid comprising a nucleotide sequence encoding a polypeptide having an amino acid sequence with 95% or greater sequence identity to an amino acid sequence selected from the group consisting of SEQ ID NO:10 and SEQ ID NO:11;
(b) producing a plant from the plant cells.

11. The method of claim 10, wherein the sequence identity is 99% or greater.

12. The method of claim 10, wherein the modulation is an increase.

13. The method of claim 10, wherein the modulation is a decrease.

14. The method of claim 10, wherein the flavonoid is a proanthocyanidin or an anthocyanidin.

15. The method of claim 10, wherein the isolated nucleic acid is operably linked to a regulatory region.

16. The method of claim 15, wherein the regulatory region is a promoter.

17. The method of claim 16, wherein the promoter is a cell-specific or tissue specific promoter.

18. The method of claim 17, wherein the tissue specific promoter is a seed-specific promoter.

19. The method of claim 18, wherein the seed-specific promoter is a vicilin promoter.

20. A cacao plant comprising an exogenous nucleic acid, the exogenous nucleic acid comprising a regulatory region operably linked to a nucleic acid encoding a flavonoid-modulating polypeptide, wherein the flavonoid-modulating polypeptide comprises an amino acid sequence having 95% or greater sequence identity to an amino acid sequence selected from the group consisting of SEQ ID NO:10 and SEQ ID NO:11, wherein a plant produced from the plant cell has a different flavonoid level compared to the corresponding level in a corresponding control plant that does not comprise the nucleic acid.

21. The method of claim 20, wherein the sequence identity is 99% or greater.

22. The method of claim 20, wherein the modulation is an increase.

23. The method of claim 20, wherein the modulation is a decrease.

24. The method of claim 20, wherein the flavonoid is a proanthocyanidin or an anthocyanidin.

25. The method of claim 20, wherein the regulatory region is a promoter.

26. The method of claim 25, wherein the promoter is a cell-specific or tissue specific promoter.

27. The method of claim 26, wherein the tissue specific promoter is a seed-specific promoter.

28. The method of claim 27, wherein the seed-specific promoter is a vicilin promoter.

* * * * *

SEQUENCE LISTING

<160> NUMBER OF SEQ ID NOS: 14

<210> SEQ ID NO 1
<211> LENGTH: 1011
<212> TYPE: DNA
<213> ORGANISM: Theobroma cacao

<400> SEQUENCE: 1

```
atggccagcc agaccgtagg caaaaagacc gcttgtgtcg taggtggcac cggatacgtt      60
gcatctttgt tggtcaagct gttgcttgag aagggctacg ctgttaacac tactgtcagg     120
gacccagaca accagaaaaa gatccctcac ctcgtaacac tacaaaagct aggagacttg     180
aaaatctttc gagcagattt gactgatgaa ggcagccttg atgtccccat agctggttgt     240
gaccttgtct tccatgttgc aacacccgtc aattttgctt ctcaagatcc tgagaatgac     300
atgatcaaac cagcaatcca gggagtgctg aacgttttga agcttgtgc caaagcaaaa      360
acagtcaaac gggtcgtctt gacttcttca gccgcagctg tgtctatcaa cacactcaag     420
gggacagatc tggtcctgac tgagaaagac tggaccgacg ttgagttctt atcgtcggca     480
aagccaccaa cttgggggta ccctgcatcc aagacattgg ctgaaaaggc agcatggaaa     540
tttgctcaag aaaacaacat cgatctcatc acggtcatcc cttctctcat gaccggtcct     600
tctctcaccc cagacgtgcc cagcagcatt ggccttgcca catctttgct ttcaggcaac     660
gaattccttg taaatgcttt gaaaggtatg caaatgttgt caggttcaat ctctatcact     720
catgtggagg acgtctgtcg ggcccatgtt tttctggcag aaaaagaatc tgcatccggc     780
cgatatatat gctgtgctgt caattccagt gttcctgagc ttgctaagtt cctcaaccaa     840
agatacctg agttcaaagt ccctactgat tttggagatt tcccctctaa agccaagttg      900
atcatttcct cggataagct tattaatgaa ggattcagct ttaagtttgg gattgaggaa     960
atctacgacc aaactgtaga atacatgaac gctaaggggc tgctcaagtg a             1011
```

<210> SEQ ID NO 2
<211> LENGTH: 336
<212> TYPE: PRT
<213> ORGANISM: Theobroma cacao

<400> SEQUENCE: 2

```
Met Ala Ser Gln Thr Val Gly Lys Lys Thr Ala Cys Val Val Gly Gly
1               5                   10                  15

Thr Gly Tyr Val Ala Ser Leu Leu Val Lys Leu Leu Leu Glu Lys Gly
            20                  25                  30

Tyr Ala Val Asn Thr Thr Val Arg Asp Pro Asp Asn Gln Lys Lys Ile
        35                  40                  45

Pro His Leu Val Thr Leu Gln Lys Leu Gly Asp Leu Lys Ile Phe Arg
    50                  55                  60

Ala Asp Leu Thr Asp Glu Gly Ser Leu Asp Val Pro Ile Ala Gly Cys
65                  70                  75                  80

Asp Leu Val Phe His Val Ala Thr Pro Val Asn Phe Ala Ser Gln Asp
                85                  90                  95

Pro Glu Asn Asp Met Ile Lys Pro Ala Ile Gln Gly Val Leu Asn Val
            100                 105                 110

Leu Lys Ala Cys Ala Lys Ala Lys Thr Val Lys Arg Val Val Leu Thr
        115                 120                 125

Ser Ser Ala Ala Ala Val Ser Ile Asn Thr Leu Lys Gly Thr Asp Leu
    130                 135                 140
```

```
Val Leu Thr Glu Lys Asp Trp Thr Asp Val Glu Phe Leu Ser Ser Ala
145                 150                 155                 160

Lys Pro Pro Thr Trp Gly Tyr Pro Ala Ser Lys Thr Leu Ala Glu Lys
                165                 170                 175

Ala Ala Trp Lys Phe Ala Gln Glu Asn Asn Ile Asp Leu Ile Thr Val
            180                 185                 190

Ile Pro Ser Leu Met Thr Gly Pro Ser Leu Thr Pro Asp Val Pro Ser
        195                 200                 205

Ser Ile Gly Leu Ala Thr Ser Leu Leu Ser Gly Asn Glu Phe Leu Val
    210                 215                 220

Asn Ala Leu Lys Gly Met Gln Met Leu Ser Gly Ser Ile Ser Ile Thr
225                 230                 235                 240

His Val Glu Asp Val Cys Arg Ala His Val Phe Leu Ala Glu Lys Glu
                245                 250                 255

Ser Ala Ser Gly Arg Tyr Ile Cys Cys Ala Val Asn Ser Ser Val Pro
                260                 265                 270

Glu Leu Ala Lys Phe Leu Asn Gln Arg Tyr Pro Glu Phe Lys Val Pro
            275                 280                 285

Thr Asp Phe Gly Asp Phe Pro Ser Lys Ala Lys Leu Ile Ile Ser Ser
290                 295                 300

Asp Lys Leu Ile Asn Glu Gly Phe Ser Phe Lys Phe Gly Ile Glu Glu
305                 310                 315                 320

Ile Tyr Asp Gln Thr Val Glu Tyr Met Asn Ala Lys Gly Leu Leu Lys
                325                 330                 335

<210> SEQ ID NO 3
<211> LENGTH: 336
<212> TYPE: PRT
<213> ORGANISM: Theobroma cacao

<400> SEQUENCE: 3

Met Ala Ser Gln Thr Val Gly Lys Lys Thr Ala Cys Val Val Gly Gly
1               5                   10                  15

Thr Gly Tyr Val Ala Ser Leu Leu Val Lys Leu Leu Leu Glu Lys Gly
                20                  25                  30

Tyr Ala Val Asn Thr Thr Val Arg Asp Pro Asp Asn Gln Lys Lys Ile
            35                  40                  45

Pro His Leu Val Thr Leu Gln Lys Leu Gly Asp Leu Lys Ile Phe Arg
        50                  55                  60

Ala Asp Leu Thr Asp Glu Gly Ser Phe Asp Val Pro Ile Ala Gly Cys
65                  70                  75                  80

Asp Leu Val Phe His Val Ala Thr Pro Val Asn Phe Ala Ser Gln Asp
                85                  90                  95

Pro Glu Asn Asp Met Ile Lys Pro Ala Ile Gln Gly Val Leu Asn Val
            100                 105                 110

Leu Lys Ala Cys Ala Lys Ala Lys Thr Val Lys Arg Val Val Leu Thr
        115                 120                 125

Ser Ser Ala Ala Ala Val Ser Ile Asn Thr Leu Glu Gly Thr Asp Leu
    130                 135                 140

Val Leu Thr Glu Lys Asp Trp Thr Asp Val Glu Phe Leu Ser Ser Ala
145                 150                 155                 160

Lys Pro Pro Thr Trp Gly Tyr Pro Ala Ser Lys Thr Leu Ala Glu Lys
                165                 170                 175

Ala Ala Trp Lys Phe Ala Gln Glu Asn Asn Ile Asp Leu Ile Thr Val
            180                 185                 190
```

```
Ile Pro Ser Leu Met Thr Gly Pro Ser Leu Thr Pro Asp Val Pro Ser
        195                 200                 205

Ser Ile Gly Leu Ala Thr Ser Leu Leu Ser Gly Asn Glu Phe Leu Val
    210                 215                 220

Asn Ala Leu Lys Gly Met Gln Met Leu Ser Gly Ser Ile Ser Ile Thr
225                 230                 235                 240

His Val Glu Asp Val Cys Arg Ala His Val Phe Leu Ala Glu Lys Glu
                245                 250                 255

Ser Gly Ser Gly Arg Tyr Ile Cys Cys Ala Val Asn Ser Ser Val Pro
            260                 265                 270

Glu Leu Ala Lys Phe Leu Asn Gln Arg Tyr Pro Glu Phe Lys Val Pro
        275                 280                 285

Thr Asp Phe Gly Asp Phe Pro Ser Lys Ala Lys Leu Ile Ile Ser Ser
    290                 295                 300

Asp Lys Leu Ile Asn Glu Gly Phe Ser Phe Lys Phe Gly Ile Glu Glu
305                 310                 315                 320

Ile Tyr Asp Gln Thr Val Glu Tyr Met Asn Ala Lys Gly Leu Leu Lys
                325                 330                 335
```

<210> SEQ ID NO 4
<211> LENGTH: 4872
<212> TYPE: DNA
<213> ORGANISM: Theobroma cacao

<400> SEQUENCE: 4

```
atgctcgatt ggcatgaaaa acacatcaag cccatgcaca ttaaagaaat gcggaatatg      60
tcaaattcta agacatggat tctccaccat ggagaaatcc aatggtttcc ggggtgtttt     120
tacatcttcc ataggtaaaa gagctttaga gtgtattgag cttgatgaag agaaccgatg     180
tctaagaaag gctctggtag tgtgcagggt aattgctgga agggttcaaa accctttaga     240
aaatgcgcaa gaaatggcaa gtcaatcaag ctttgattca ctggctggaa actttgatag     300
ccactcgaat attgaggaac tctattcact aaatcctaga gctctcttcc cttgttttgt     360
ggtcatctgc aaaccctcaa agcaaagtgc tcaaaaatta aacttagga ccacgttcct      420
tgtcattgtg attgtgaggt ctaatttctt tatccaacct tctctgtaat tatttgttct     480
tatagtaaat atatcttctc tttctgcaag gtatttgttc tctcaaaact tcatcttgaa     540
ccgctatgag attgcatcaa tctacataga gctgtagcta gtctagctgc ttgaagtttc     600
tgaccagcct tctcttgcac cgcaccctct ctctctctcc cctcatttt ctagtgaaac      660
tgccccgagg attgaattct gttctgcaga taagtcaaat ttgaccatca atcaagctcc     720
tatccattaa ttctgcttgc ttatatccct tttagacaaa tgtaattaat aacacaaacc     780
ctagtacaga atctattaag tctaatttga attcaatcct ggaagtgcac tgatcctgct     840
atgcgtggtc taattcgtca acaacattgt cccctcttct ttctgtctgc actgtcttgt     900
cactactatg gctcttcttg ggctcagatc taatcctgat actgtgtttt gataataaga     960
gttgcttaca gatacgagtt agggtattta attacagacc tattcgggaa ggggaaggga    1020
aacttgttac aatgtactta acaaagatcg tcaggatatc tccgggtgtt ctttgatcct    1080
cctatgggt taatcttatg tttcctcgat taaacaaatg aaaaaataaa taataaagg      1140
attcctggca acagttctct gttgcttgcc tataattgaa attgtgaatc ataagaagta    1200
aaaccaccta accacaggcc cacgtgaggc atcatttgga gcaacttgag gtttggccag    1260
ctacccctct tttgccttcc aaagatttta acttgacatc agttgagcct tcacttccaa    1320
```

```
catttcagca aacttcatct actgtttttc tgcaccactg catgtcctat atgatatcca  1380
aaaaacaact ccccctttct aacatacaat aaattttgtg ctcgaaatct gattatcgct  1440
tatgatcatt actggaagat gccaagctcc aaaacttcac ctaaatgctt ttgtgtgcct  1500
cttcttaagt ccatactttc ttagtaaaag aatgtggatg caaaaaccca ttttgggaat  1560 actttccac agtaaaaaaa aaaattatta gattatgtct tgattcaatc aaaattcctc  1620
aatgaaccat agaacaattt tagtgactaa agcagttgat aaatactcaa cccatttact  1680
attatttaat ggttttctca tagaacaatt ttttaagaag tacacaagca ataaactcta  1740
catttactct acatttatca atcgaataca aaactatatt ttggtagggg gtcactgtta  1800
actcagtcat tatcaaaaga agcgatgaga ggaaatgagt ttctagctaa aaagaaactc  1860
gtgggtactg actggctacc ccttgtagta gcagtttggg gagtcgagtc acaccaccga  1920
tggtttgaaa gacttttga gtcgttggta tgcacaaggg cacgtgctca ccttctccat  1980
ctaaaaatct actcaagccc tgggtaagtg cccatcgtct ataaacaat aatgcaataa  2040 gtttattcca cctatgcatc tttgtctgaa cggttgaagg gttcaaaaca agcccaaaaa  2100
atcgaaacgg aaaagcaaaa gtaaggtacc cggtcaagaa aaggaatata gtcattgaag  2160
ccatggccag ccagaccgta ggcaaaaaga ccgcttgtgt cgtaggtggc accggatacg  2220
ttgcatcttt gttggtcaag ctgttgcttg agaagggcta cgctgttaac actactgtca  2280
gggacccagg ttgatcttct cttcttcttc atcttcttct gttttcttg ttcatttgtt  2340 tctactgctt tgctttggtg ggtcatccca gtatttact ttcttcccct tccttggttt  2400
tcttgttttt atatataata tattggtatg gctgctgctg caatttagga atttctacga  2460
tttatgcccc cattgtagca ttagttcttt gttctttgtt ttttcacttt aagcttaaac  2520
tataaattcc tacctactct gtatcgagca tgttggaagt taataagcga gaacaaccga  2580
ggaacatacc gccttgtctt gtcagttggt gtttttagg gggtacccac gatatccgtt  2640
gcctgagcag gagagaatac tatcaattcc ttgggtttga gttcacccct ctcgaagagt  2700
ttccttacca aattaatcac attttttgca gataaagtgt aatgagtaga atcttttttt  2760
cttttttctt tttgggggtt tattttcatt ttctggcaac acccagagta agtaaacatg  2820
aatgggtgta atgctgtgtc ttttctgcag acaaccagaa aaagatccct cacctcgtaa  2880
cactacaaaa gctaggagac ttgaaaatct ttcgagcaga tttgactgat gaaggcagct  2940
ttgatgtccc catagctggt tgtgaccttg tcttccatgt tgcaacaccc gtcaattttg  3000
cttctcaaga tcctgaggta tgtaaaacca ttaaactgct tttccagtga tgatcaaatt  3060
ccttctggtt ttgaggaatg atgacaaggt ttactttatt ggattttgat tatagaatga  3120
catgatcaaa ccagcaatcc agggagtgct gaacgttttg aaagcttgtg ccaaagcaaa  3180
aacagtcaaa cgggtcgtct tgacttcttc agccgcagct gtgtctatca acacactcga  3240
ggggacagat ctggtcctga ctgagaaaga ctggaccgac gttgagttct tatcgtcggc  3300
aaagccacca acttgggtaa caattttcat gctaatccat tcctctttct cttatcttcg  3360
ggggaattgc agaagagggc aaggtaacaa aaataattgg tgtgcataat ctgaagtaag  3420
cttttatcca tgaatgcagg ggtaccctgc atccaagaca ttggctgaaa aggcagcatg  3480
gaaatttgct caagaaaaca acatcgatct catcacggtc atcccttctc tcatgaccgg  3540
tccttctctc accccagacg tgcccagcag cattggcctt gccacatctt tgctttcagg  3600
tattaagtta gaacctcgtg tcctggcctt gtttctagat gtaaaactga tgcataaaga  3660
```

-continued

```
agtagcctgg agcaccatga actgtaactg atgggaattt taacattttt gcaggcaacg    3720
aattccttgt aaatgctttg aaaggtatgc aaatgttgtc aggttcaatc tctatcactc    3780
atgtggagga cgtctgtcgg gcccatgtct ttctggcaga aaaagaatct ggatccggcc    3840
gatatatatg cctgtgctgt caattccagt gttcctgagc ttgctaagtt cctcaaccaa    3900
agatacsctg agttcaaagt ccctactgag taagccaacc tgcattcaat atcacaatct    3960
aaacttctct tctttctgct agaattgtgg ttaatcttag ttttgtttgc tttgttacaa    4020
ttgcagtttt ggagatttcc cctctaaagc caagttgatc atttcctcgg ataagcttat    4080
taatgaagga ttcagcttta agtttgggat tgaggaaatc tacgaccaaa ctgtagaata    4140
catgaacgct aaggggctgc tcaagtgaag agtccgccta acattgtccc taatgactgt    4200
gatgtttggt tgcttaagat gtatgctgtc ttttgttata ttatcctaat aacttgatgt    4260
tctgcaaatc aagcaaatac catatggcga atatcatttg ctttcccaaa agaaaaagaa    4320
aaaaaaaaaa gaaatccaaa gtatcctatt tagtattgga agaccaaaaa tcaaatcacc    4380
aactgaatca tggaatgggt tcttgtgtac ttatcaaatg actatcatac tttccttctg    4440
cgtccaattc ttcaacgttc aattaaagaa ggatcaacag tcccttgtag atccagtttg    4500
aaagttgatc ttcaaaaaaa aaaaaatcca gtttgaaagt agtttcctct gctttagcag    4560
gtggttttgc ccatgttgca cccttgagtt tcttggcttg tgggtctcgg acaatgtcag    4620
cacgatgtcc ctcattgagg ccttttcct ggagacagga ttgatacaag tataagcaag    4680
ggcagccata tgattcagtt gttgaacatc aaatgttcct tgaagtcgag gatctgcaat    4740
ctcttcccac cctacatcgt tttccacatc aatagccgcc tattcatgat cacagaaaca    4800
agaaaaatga tattgaatca ttcatgtttt gtgcatgcat aggcactcaa aatcaggtga    4860
gcaaagagca ga                                                       4872
```

<210> SEQ ID NO 5
<211> LENGTH: 1065
<212> TYPE: DNA
<213> ORGANISM: Theobroma cacao

<400> SEQUENCE: 5

```
atggtgactt caatggcccc cagagtagag agcttggcaa gcagtgggat tcagtccatc      60
ccgaaggagt acattagacc tcaggaagag cttacaagca ttggtaatgt gttttgaagaa    120
gagaaaaaag aggaagggcc tcaggttcca accattgatt taaaggaaat tgactcagag    180
gacagagagg tacgggagag atgtcgccag gagttgaaga gagctgccac ggagtggggt    240
gtgatgcacc ttgttaacca tgggatctcg gacgagctca tggaacgtgt caagaaagct    300
ggacagaagt tctttgaact ttctgtcgag gagaaagaga agtatgccaa cgaccagact    360
ttggggaaga ttcaggggta tggcagcaag ctagctaaca atgctagtgg tcagcttgag    420
tgggaggact acttcttcca tcttgtgtat cccgaggaca agagagactt gtccatctgg    480
cctcaaacac caagcgacta cactgaagtc acaagtgagt acgcaaggca actccgagtc    540
cttgcgagca aaattctttc ggcactatca cttgcttag gattggaaga aggaaggcta    600
gagaaggaag ttggtggatt ggaagagctc cttcttcaaa tgaaaatcaa ttactatccc    660
aaatgccctc aaccagaact cgctctcggt gtggaagctc acacagatgt aagtgcactt    720
accttcattc tccacaacat ggtccctggc ctgcaacttt tctacgaagg caagtggatc    780
accgcaaaat gtgttccaaa ctccatcatc atgcacattg gtgacaccgt cgagatcctc    840
agcaatggta agtacaagag cattcttcac aggggtctgg ttaacaagga gaaggttagg    900
```

-continued

```
atctcatggg cagttttctg tgagccgcca aaggagaaga tcattctcaa gccactgcca    960
gagactgtgt ccgagacgga gcctccgttg ttccctcctc gcacctttgc tcagcatatt   1020
caccacaagc tgtttaggaa gacccaggat ggcctgtcta attga                    1065
```

<210> SEQ ID NO 6
<211> LENGTH: 354
<212> TYPE: PRT
<213> ORGANISM: Theobroma cacao

<400> SEQUENCE: 6

```
Met Val Thr Ser Met Ala Pro Arg Val Glu Ser Leu Ala Ser Ser Gly
1               5                   10                  15

Ile Gln Ser Ile Pro Lys Glu Tyr Ile Arg Pro Gln Glu Glu Leu Thr
            20                  25                  30

Ser Ile Gly Asn Val Phe Glu Glu Lys Glu Glu Gly Pro Gln
        35                  40                  45

Val Pro Thr Ile Asp Leu Lys Glu Ile Asp Ser Glu Asp Arg Glu Val
    50                  55                  60

Arg Glu Arg Cys Arg Gln Glu Leu Lys Arg Ala Ala Thr Glu Trp Gly
65                  70                  75                  80

Val Met His Leu Val Asn His Gly Ile Ser Asp Glu Leu Met Glu Arg
                85                  90                  95

Val Lys Lys Ala Gly Gln Lys Phe Phe Glu Leu Ser Val Glu Glu Lys
            100                 105                 110

Glu Lys Tyr Ala Asn Asp Gln Thr Leu Gly Lys Ile Gln Gly Tyr Gly
        115                 120                 125

Ser Lys Leu Ala Asn Asn Ala Ser Gly Gln Leu Glu Trp Glu Asp Tyr
    130                 135                 140

Phe Phe His Leu Val Tyr Pro Glu Asp Lys Arg Asp Leu Ser Ile Trp
145                 150                 155                 160

Pro Gln Thr Pro Ser Asp Tyr Thr Glu Val Thr Ser Glu Tyr Ala Arg
                165                 170                 175

Gln Leu Arg Val Leu Ala Ser Lys Ile Leu Ser Ala Leu Ser Leu Cys
            180                 185                 190

Leu Gly Leu Glu Glu Gly Arg Leu Glu Lys Glu Val Gly Gly Leu Glu
        195                 200                 205

Glu Leu Leu Leu Gln Met Lys Ile Asn Tyr Tyr Pro Lys Cys Pro Gln
    210                 215                 220

Pro Glu Leu Ala Leu Gly Val Glu Ala His Thr Asp Val Ser Ala Leu
225                 230                 235                 240

Thr Phe Ile Leu His Asn Met Val Pro Gly Leu Gln Leu Phe Tyr Glu
                245                 250                 255

Gly Lys Trp Ile Thr Ala Lys Cys Val Pro Asn Ser Ile Ile Met His
            260                 265                 270

Ile Gly Asp Thr Val Glu Ile Leu Ser Asn Gly Lys Tyr Lys Ser Ile
        275                 280                 285

Leu His Arg Gly Leu Val Asn Lys Glu Lys Val Arg Ile Ser Trp Ala
    290                 295                 300

Val Phe Cys Glu Pro Pro Lys Glu Lys Ile Ile Leu Lys Pro Leu Pro
305                 310                 315                 320

Glu Thr Val Ser Glu Thr Glu Pro Pro Leu Phe Pro Pro Arg Thr Phe
                325                 330                 335

Ala Gln His Ile His His Lys Leu Phe Arg Lys Thr Gln Asp Gly Leu
```

```
                      340                 345                 350
Ser Asn

<210> SEQ ID NO 7
<211> LENGTH: 354
<212> TYPE: PRT
<213> ORGANISM: Theobroma cacao

<400> SEQUENCE: 7

Met Val Thr Ser Met Ala Pro Arg Val Glu Ser Leu Ala Ser Ser Gly
1               5                   10                  15

Ile Gln Ser Ile Pro Lys Glu Tyr Ile Arg Pro Gln Glu Glu Leu Thr
            20                  25                  30

Ser Ile Gly Asn Val Phe Glu Glu Lys Lys Glu Glu Gly Pro Gln
        35                  40                  45

Val Pro Thr Ile Asp Leu Lys Glu Ile Asp Ser Glu Asp Arg Glu Val
    50                  55                  60

Arg Glu Arg Cys Arg Gln Glu Leu Lys Lys Ala Ala Thr Glu Trp Gly
65                  70                  75                  80

Val Met His Leu Val Asn His Gly Ile Ser Asp Glu Leu Met Glu Arg
                85                  90                  95

Val Lys Lys Ala Gly Gln Lys Phe Phe Glu Leu Ser Val Glu Glu Lys
            100                 105                 110

Glu Lys Tyr Ala Asn Asp Gln Ala Leu Gly Lys Ile Gln Gly Tyr Gly
        115                 120                 125

Ser Lys Leu Ala Asn Asn Ala Ser Gly Gln Leu Glu Trp Glu Asp Tyr
    130                 135                 140

Phe Phe His Leu Val Tyr Pro Glu Asp Lys Arg Asp Leu Ser Ile Trp
145                 150                 155                 160

Pro Gln Thr Pro Ser Asp Tyr Thr Glu Val Thr Ser Glu Tyr Ala Arg
                165                 170                 175

Gln Leu Arg Val Leu Ala Ser Lys Ile Leu Leu Ala Leu Ser Leu Cys
            180                 185                 190

Leu Gly Leu Glu Glu Gly Arg Leu Glu Lys Glu Val Gly Gly Leu Glu
        195                 200                 205

Glu Leu Leu Leu Gln Met Lys Ile Asn Tyr Tyr Pro Lys Cys Pro Gln
    210                 215                 220

Pro Glu Leu Ala Leu Gly Val Glu Ala His Thr Asp Val Ser Ala Leu
225                 230                 235                 240

Thr Phe Ile Leu His Asn Met Val Pro Gly Leu Gln Leu Phe Tyr Glu
                245                 250                 255

Gly Lys Trp Ile Thr Ala Lys Cys Val Pro Asn Ser Ile Ile Met His
            260                 265                 270

Ile Gly Asp Thr Ile Glu Ile Leu Ser Asn Gly Lys Tyr Lys Ser Ile
        275                 280                 285

Leu His Arg Gly Leu Val Asn Lys Glu Lys Val Arg Ile Ser Trp Ala
    290                 295                 300

Val Phe Cys Glu Pro Pro Lys Glu Lys Ile Ile Leu Lys Pro Leu Pro
305                 310                 315                 320

Glu Thr Val Ser Glu Thr Glu Pro Pro Leu Phe Pro Pro Arg Thr Phe
                325                 330                 335

Ala Gln His Ile His His Lys Leu Phe Arg Lys Thr Gln Asp Gly Leu
            340                 345                 350

Ser Asn
```

<210> SEQ ID NO 8
<211> LENGTH: 3939
<212> TYPE: DNA
<213> ORGANISM: Theobroma cacao

<400> SEQUENCE: 8

| | | | | | | |
|---|---|---|---|---|---|---|
| tatatatata | tatatatata | tatatatata | tatatatata | tatatatata | tattgtgtgg | 60 |
| aaaaactaaa | aggcttttac | tcttctggtc | aagaacaaga | agaatgggca | agcaccaaaa | 120 |
| aagcaaaaaa | gtctttgttc | cccttctttt | gttcgacctg | tttatcccat | agttcatata | 180 |
| aaatcacatt | tttggccaat | tttttaggga | cgaagaaaca | aggaacggag | gccaaggcaa | 240 |
| gataggggcc | ggtggttttg | ctagcaaata | catacgaaaa | ttaattgaac | taggtagcag | 300 |
| caggcatata | tcctgctgac | tgaaagctcg | tagagatgaa | gcacgagcaa | ccaactacct | 360 |
| cattgttctt | ccagaagcaa | ctcctagttt | cgatcccatg | caagatcttc | aatcatataa | 420 |
| cgtctagaac | tttcttcttt | cgtacataat | aagtaatgtt | caaatcaac | catttgttaa | 480 |
| aagcaaaacc | atatggaata | atattgaatt | aaacctattt | aaatttcaat | tgaagctttt | 540 |
| ttcggaatga | atggtccata | aactagactt | tctaatgctt | agactaacaa | ggtgtatata | 600 |
| tatatatatg | ttaagagtat | ataatttga | tcattttat | tcgttattaa | aaatatattt | 660 |
| tacaagtttt | attactttat | aatatataat | ataaaacgaa | aggagtatta | ttattcataa | 720 |
| aaaaaagaaa | tccaattctc | atctcatcta | tgcattgttg | agtcaaggcc | ttaatgtttt | 780 |
| ttgagttcaa | tcaaacttta | atgtttccaa | aaagagggca | ggggagggat | tcaattaact | 840 |
| ccgctaatga | tgattagctg | ttgaaatcat | ttgagtcctc | tctgccattt | ggggttaaat | 900 |
| gaatccaaat | taagatgggt | tagatgaaac | gtgcagtcct | ggcttggtag | ttggacttc | 960 |
| caagtagaaa | ttttggtcgt | tatttatccg | cgctctgctt | aattaattag | tcaactctcc | 1020 |
| tgtaaagcaa | atcagctaat | ttgcttaaac | tacccattac | tactatgtac | attagctcaa | 1080 |
| gaaatgtgca | ctttaggcat | tgctccattg | cctggtgtaa | attaagttaa | agtacaaagt | 1140 |
| gacttaatag | aaagagtgtt | tattatgaca | ttattaatac | ttttaatttc | tctcaaataa | 1200 |
| cattatttaa | gacatggata | attaacttt | atgtatgtat | aatcttttca | ttttataaaa | 1260 |
| gttaaaccat | tgataaacag | gttatctagc | atggttcaaa | aaaacagtaa | gtaatttaga | 1320 |
| atagtacaat | ttaatattta | aattaagaga | tattgaaaac | ttatatagta | ttagatgtat | 1380 |
| atattgaaca | ttaattactt | gttgaatgga | tgttttcatt | tttacatata | attttaggtt | 1440 |
| cacaagaatt | atatgatgaa | tggaaaagaa | acaaaagcaa | aacaagttct | acctcacagg | 1500 |
| cgcgtttggt | tgagatagat | tagcaaatta | gagcagaggg | tgttaggtcc | aagcttccag | 1560 |
| tcaactcacc | ttgggacaac | caagttgta | tgaccactgc | tctaactcag | accttggtgg | 1620 |
| agctcatcac | gtgtatgact | taccagttac | atctattttt | cttcagtatt | tctttctctt | 1680 |
| gatttggtag | ctctacccca | tttgcatgtt | cactaaggca | actgattttt | tttttttta | 1740 |
| atatcatagc | tttcttgatc | ttccgtgtta | aaattttctc | gaaccagatc | attataaaaa | 1800 |
| ggccactaaa | gatcagcact | acggtatatt | cctgagagtg | aggttcacca | caaaagcaaa | 1860 |
| aaaaaaaaaa | aagggttgtt | gttacagagt | ggaaacaagg | aacttctaaa | acaagtttag | 1920 |
| aagatcgcaa | gaatggtgac | ttcaatggcc | cccagagtag | agagcttggc | aagcagtggg | 1980 |
| attcagtcca | tcccgaagga | gtacattaga | cctcaggaag | agcttacaag | cattggtaat | 2040 |
| gtgtttgaag | aagagaaaaa | agaggaaggg | cctcaggttc | caaccattga | tttaaaggaa | 2100 |

-continued

```
attgactcag aggacagaga ggtacgggag agatgtcgcc aggagttgaa gaaagctgcc    2160
acggagtggg gtgtgatgca ccttgttaac catgggatct cggacgagct catggaacgt    2220
gtcaagaaag ctggacagaa gttctttgaa cttcctgtcg aggagaaaga gaagtatgcc    2280
aacgaccagg cttgggggaa gattcagggg tatggcagca agctagctaa caatgctagt    2340
ggtcagcttg agtgggagga ctacttcttc catcttgtgt atcccgagga caagagagac    2400
ttgtccatct ggcctcaaac accaagcgac tacacgtgag tttatggctt ttggtttatt    2460
ttacatactg cttttttgcaa ttactagatt ctttgatcga ttaatgttaa tgtttcttga    2520
gcatcatatc aaacaagctg tatatgtcca ccgggttcat tgaacactat cacaattttt    2580
tttttaaaag tgaaaacttt cacatttaat aaaaagatct acaaggttgg caattatctg    2640
tctgcctgat tagatagaaa attttcctaa tattcaggat acttattaca gtaagaacaa    2700
tatttctgtg atatgaaata ttaaagttaa acgtaaacta tccgtatgga ttttaacaat    2760
tcaccactgt tcattggtta ctatgcagtg aagtcacaag tgagtacgca aggcaactcc    2820
gagtccttgc gagcaaaatt cttttggcac tatcactttg cttaggattg gaagaaggaa    2880
ggctagagaa ggaagttggt ggattggaag agctccttct tcaaatgaaa atcaattact    2940
atcccaaatg ccctcaacca gaactcgctc tcggtgtgga agctcacaca gatgtaagtg    3000
cacttacctt cattctccac aacatggtcc ctggcctgca actttctac gaaggcaagt    3060 ggatcaccgc aaaatgtgtt ccaaactcca tcatcatgca cattggtgac accatcgaga    3120
tcctcagcaa tggtaagtac aagagcattc ttcacagggg tctggttaac aaggagaagg    3180
ttaggatctc atgggcagtt ttctgtgagc cgccaaagga gaagatcatt ctcaagccac    3240
tgccagagac tgtgtccgag acggagcctc cgttgttccc tcctcgcacc tttgctcagc    3300
atattcacca caagctgttt aggaagaccc aggatggcct gtctaattga ggctagtcat    3360
tagttaaatt aaaaatatct tcttgttttt aacgtcttta taagctgttt acgggtctgg    3420
tgatgctata ttatcttggg ttaaaccttt ggttgtggta ggctgatgcc ggggtggtgt    3480
ctgtctttca ctccttggct tctctttacc tgctttattg aataatggca gactgatttg    3540
cttccttgtg ttaagcagtt tgtgaattaa tggtctttgt ttacatttct ttcctcaatt    3600
tacgtctcca taaacagaac tcttttcccct ccacactttc cttcttagtc taaatttttt    3660
aatacaatag caatctttt cttaaacaaa tcaagtgaag tacctgtaat tatctaagta    3720
gtgaatcaaa ccctaaacag gcaagttttt gcctcccttc cgttcttttt attccgaaca    3780
cccaggaaat taacaaaagg taaattgtcc ccagtggcac tcggttaatt gtcgtttaga    3840
ttttgatatg tataactttg tgttgggggc attttctgcc ctgtgaaggt caagcagcca    3900
tgctaacagt ataactatta agtagtctca ataatgaag                          3939
```

<210> SEQ ID NO 9
<211> LENGTH: 1086
<212> TYPE: DNA
<213> ORGANISM: Theobroma cacao

<400> SEQUENCE: 9

```
atggatatga atcaacaaa catgaatggt tcctctccta atgtctcgga agaaactggt      60
cggaccttag tcgttggttc gggtgggttt atgggccggt tcgtcaccga agccagccta    120
gactccggcc gtcctacgta tattttggct cggtctagtt cgaactctcc ttccaaagcc    180
tccaccatca agtttcttca agacagagga gccactgtta tttacggctc tatcacagac    240
aaagaattca tggagaaggt tctgaaagaa cataagatag aagttgtaat atctgcagtg    300
```

-continued

```
ggaggggaa gcatcttaga ccagttcaat ctgatagagg ctatcaggaa tgttgacact    360
gtcaagaggt tcttaccgtc tgaattcggg cacgacacag acagggctga cccggtggag    420
ccagggctga ccatgtatga acaaagagg cagattagga ggcaggtaga gaaatctggg    480
attccttaca cttacatatg ttgcaattcc attgcagctt ggccctacca cgacaacact    540
caccctgcag atgttctgcc acccttgat aggttcaaaa tatacggtga tggcactgtc    600
aaagcatact ttgtggcggg taccgatatt gggaagttca ctataatgtc gatagaagat    660
gatcgaacac tgaacaaaac tgtccatttt caacctccaa gcaacctact aaacataaac    720
gagatggcct cactatggga ggagaagatt ggacgtacac ttcctagggt caccatcaca    780
gaagaagatc tgctgcagat ggccaaagag atgcggatcc cacagagtgt ggttgcagca    840
ttaactcatg atattttcat aaatggctgc caaataaact ttagcttgga caagccaact    900
gatgttgaag tctgctccct ctacccagac actcctttc gaaccatcaa cgagtgcttc    960
gaggactttg ccaagaagat aattgataat gccaaagcag tgagcaagcc agcggcaagc   1020
aacaatgcaa tatttgtgcc aactgctaag ccaggagcat tgcctatcac tgcgatatgc   1080
acatga                                                              1086
```

<210> SEQ ID NO 10  
<211> LENGTH: 359  
<212> TYPE: PRT  
<213> ORGANISM: Theobroma cacao

<400> SEQUENCE: 10

```
Met Lys Ser Thr Asn Met Asn Gly Ser Ser Pro Asn Val Ser Glu Glu
1               5                   10                  15

Thr Gly Arg Thr Leu Val Val Gly Ser Gly Phe Met Gly Arg Phe
            20                  25                  30

Val Thr Glu Ala Ser Leu Asp Ser Gly Arg Pro Thr Tyr Ile Leu Ala
        35                  40                  45

Arg Ser Ser Ser Asn Ser Pro Ser Lys Ala Ser Thr Ile Lys Phe Leu
    50                  55                  60

Gln Asp Arg Gly Ala Thr Val Ile Tyr Gly Ser Ile Thr Asp Lys Glu
65                  70                  75                  80

Phe Met Glu Lys Val Leu Lys Glu His Lys Ile Glu Val Val Ile Ser
                85                  90                  95

Ala Val Gly Gly Gly Ser Ile Leu Asp Gln Phe Asn Leu Ile Glu Ala
            100                 105                 110

Ile Arg Asn Val Asp Thr Val Lys Arg Phe Leu Pro Ser Glu Phe Gly
        115                 120                 125

His Asp Thr Asp Arg Ala Asp Pro Val Glu Pro Gly Leu Thr Met Tyr
    130                 135                 140

Glu Gln Lys Arg Gln Ile Arg Arg Gln Val Glu Lys Ser Gly Ile Pro
145                 150                 155                 160

Tyr Thr Tyr Ile Cys Cys Asn Ser Ile Ala Ala Trp Pro Tyr His Asp
                165                 170                 175

Asn Thr His Pro Ala Asp Val Leu Pro Pro Leu Asp Arg Phe Lys Ile
            180                 185                 190

Tyr Gly Asp Gly Thr Val Lys Ala Tyr Phe Val Ala Gly Thr Asp Ile
        195                 200                 205

Gly Lys Phe Thr Ile Met Ser Ile Glu Asp Asp Arg Thr Leu Asn Lys
    210                 215                 220
```

```
Thr Val His Phe Gln Pro Pro Ser Asn Leu Leu Asn Ile Asn Glu Met
225                 230                 235                 240

Ala Ser Leu Trp Glu Glu Lys Ile Gly Arg Thr Leu Pro Arg Val Thr
            245                 250                 255

Ile Thr Glu Glu Asp Leu Leu Gln Met Ala Lys Glu Met Arg Ile Pro
        260                 265                 270

Gln Ser Val Val Ala Ala Leu Thr His Asp Ile Phe Ile Asn Gly Cys
    275                 280                 285

Gln Ile Asn Phe Ser Leu Asp Lys Pro Thr Asp Val Glu Val Cys Ser
290                 295                 300

Leu Tyr Pro Asp Thr Pro Phe Arg Thr Ile Asn Glu Cys Phe Glu Asp
305                 310                 315                 320

Phe Ala Lys Lys Ile Ile Asp Asn Ala Lys Ala Val Ser Lys Pro Ala
                325                 330                 335

Ala Ser Asn Asn Ala Ile Phe Val Pro Thr Ala Lys Pro Gly Ala Leu
                340                 345                 350

Pro Ile Thr Ala Ile Cys Thr
            355

<210> SEQ ID NO 11
<211> LENGTH: 359
<212> TYPE: PRT
<213> ORGANISM: Theobroma cacao

<400> SEQUENCE: 11

Met Lys Ser Thr Asn Met Asn Gly Ser Ser Pro Asn Val Ser Glu Glu
1               5                   10                  15

Thr Gly Arg Thr Leu Val Val Gly Ser Gly Phe Met Gly Arg Phe
            20                  25                  30

Val Thr Glu Ala Ser Leu Asp Ser Gly Arg Pro Thr Tyr Ile Leu Ala
            35                  40                  45

Arg Ser Ser Ser Asn Ser Pro Ser Lys Ala Ser Thr Ile Lys Phe Leu
        50                  55                  60

Gln Asp Arg Gly Ala Thr Val Ile Tyr Gly Ser Ile Thr Asp Lys Glu
65                  70                  75                  80

Phe Met Glu Lys Val Leu Lys Glu His Lys Ile Glu Val Val Ile Ser
                85                  90                  95

Ala Val Gly Gly Gly Ser Ile Leu Asp Gln Phe Asn Leu Ile Glu Ala
            100                 105                 110

Ile Arg Asn Val Asp Thr Val Lys Arg Phe Leu Pro Ser Glu Phe Gly
        115                 120                 125

His Asp Thr Asp Arg Ala Asp Pro Val Glu Pro Gly Leu Thr Met Tyr
130                 135                 140

Glu Gln Lys Arg Gln Ile Arg Arg Gln Ile Glu Lys Ser Gly Ile Pro
145                 150                 155                 160

Tyr Thr Tyr Ile Cys Cys Asn Ser Ile Ala Ala Trp Pro Tyr His Asp
                165                 170                 175

Asn Thr His Pro Ala Asp Val Leu Pro Pro Leu Asp Arg Phe Lys Ile
            180                 185                 190

Tyr Gly Asp Gly Thr Val Lys Ala Tyr Phe Val Ala Gly Thr Asp Ile
        195                 200                 205

Gly Lys Phe Thr Ile Met Ser Ile Glu Asp Asp Arg Thr Leu Asn Lys
    210                 215                 220

Thr Val His Phe Gln Pro Pro Ser Asn Leu Leu Asn Ile Asn Glu Met
225                 230                 235                 240
```

Ala Ser Leu Trp Glu Glu Lys Ile Gly Arg Thr Leu Pro Arg Val Thr
            245                 250                 255

Ile Thr Glu Glu Asp Leu Leu Gln Met Ala Lys Glu Met Arg Ile Pro
        260                 265                 270

Gln Ser Val Val Ala Ala Leu Thr His Asp Ile Phe Ile Asn Gly Cys
    275                 280                 285

Gln Ile Asn Phe Ser Leu Asp Lys Pro Thr Asp Val Glu Val Cys Ser
290                 295                 300

Leu Tyr Pro Asp Thr Pro Phe Arg Thr Ile Asn Glu Cys Phe Glu Asp
305                 310                 315                 320

Phe Ala Lys Lys Ile Ile Asp Asn Ala Lys Ala Val Ser Lys Pro Ala
                325                 330                 335

Ala Ser Asn Asn Ala Ile Phe Val Pro Thr Ala Lys Pro Gly Ala Leu
            340                 345                 350

Pro Ile Thr Ala Ile Cys Thr
        355

<210> SEQ ID NO 12
<211> LENGTH: 6407
<212> TYPE: DNA
<213> ORGANISM: Theobroma cacao
<220> FEATURE:
<221> NAME/KEY: modified_base
<222> LOCATION: (6385)..(6385)
<223> OTHER INFORMATION: a, c, t, g, unknown or other

<400> SEQUENCE: 12
tgagcagcac tgatgtaaat taaaaaagt ttaggactaa taaaaaaatt cattcaaaaa      60
atttggtaaa ataacaaaaa atttaccata tgacttgaag acgaaaaaaa tttgttttca    120
aaaatcaaac tccatgtgac ccaagaatca taataaaatc cctattaata atgattctca    180
cttttaattt aaaaaaaaaa aaccaacact ctatatgtaa gatagatgat aaaatttgat    240
taattcaatc tcacatgttg ggactagtaa attccataag ataatgat tcctttctga    300 caaccaatca ggaagaattt caatcaattt ttgcttaata aaaaaagatt atcctgtctg    360
ccattgttgt cagagggttt ttttttttc acagtttaag atctatgttt tatataatta    420
atgaggccat tcttctatat atatatatat atatatggag tacttgcact aatttaatct    480
catttaaatt ttaatttact aaaaaagtat atattaattt tggtccatgc ctgcacaaca    540
aaaaatatta tttctaaatt atatcgataa ttacaattta caaagctaaa ataaaataaa    600
ataaaaatta aattaaaagc ctatttggtt tgatttttt aaaacttaaa aattaatata    660
aaactcttat gaaaaataat agctttcaaa attaagttaa atctgtttgg taaatttact    720
tttataagct ctatttata gataagttgt tttgcaaaac aatttatata agttttaatt    780
ttagttaaaa ttacaatcaa gggtgtgtgt aataaataac ttttattaa tcataaattt    840 tttttagaac aataaaaaaa gttaattta ttttcttgtt catttgaaat aaaaaatata    900
aaatttataa ttaataataa atcataaaaa aagaaaaaca gataatatta aaattatttt    960
taatagataa gaacattttg aaacaaaaag aaaagttttt ccggaaaaaa tatatgtttt   1020
taaaaataga gaagagaaat ctcttctcca aaggttattt taaagctctt ttttttttgt   1080
tttgaaattt tgtttgttaa aagaaattat ttttaaaaa atttctcaaa atatctatt    1140 gacttgattt ttatttttaa gagacagata agttgaaaaa aaaaatcaaa ttaaatcggc   1200
actaaatgtt gaaaaaattt aaaattaatt actagaagaa atatttatgg gggaagaaat   1260

```
tttaatttca gaagaaaaat agaaaaaatt atatgtttga gtagctaggc acctagctgt    1320
ttttagtaga gttgacttgg gccacaatgg gaatgtgctg tctgacagtc aaggacgtgg    1380
ctatccaacc acactgtcaa tcaaaaaccc accaatcagt cttcctcctc ccctccccca    1440
gcctctttta caaagtacat acgtatattt tcttttctgt attttgtta gttatagtac     1500 aaatcaaatc gggttttaag ggaatttta atctacaaac tatttctata cacaaaatta    1560
gccatactaa ggaagaaaaa aaattaata atatagcaca ttagtaatat aaattaatta    1620
ctcgatacaa tgataaaatt gcttcagttt tacatcaaaa cttgattaaa aaaattatcg    1680 attgatttt cttttaatc tttaaattta ataattttt tcccttaaat ttaacacgat       1740
aagaatgttc gaatgagagt cggatgctag ctgaagttac taattaagaa aaaagtatac    1800 aacttttag caaaaatgaa aataggata tttggtttta ttatcctatt attcactatt      1860
ttgctaaaaa gttgtataat ttttataaaa aaaataaata aaggggggaaa aagaggataa   1920 aaaaatactc aatgctacct aataaaatgg ctacatacgg gtagacaaca actcatgcta    1980
cgaaaattgc aattccatgt tccctgttg ctaatttgcg ccattgcttt tgcttacctg     2040
cccttaattg ctaacctcta taagcaca agtccatatt gcttttggt caccgccaca       2100 ttcctcactc tctcgtcact cttttatttt tttttctgg tttcctttgt gcgccaaaac     2160
ttaagcttaa gtaaaagcaa acaatatgaa atcaacaaac atgaatggtt cctctcctaa    2220
tgtctcggaa gaaactggtc ggaccttagt cgttggttcg ggtgggttta tgggccggtt    2280
cgtcaccgaa gccagcctag actccggccg tcctacgtat attttggctc ggtctagttc    2340
gaactctcct tccaaagcct ccaccatcaa gtttcttcaa gacagaggag ccactgttat    2400
ttacgtatgt acaattctcc ctcgacacct cttccatttt ctggttacat ttccacacgt    2460
atacaaatac atatacattt ctaatgtgta attatttgtg tatatttata tatatgtaat    2520
gtataatgtg taattattta tgtatgtata tatgtatgta tgtatgtatg tatgtatata    2580
tgtatgtacg gacgttatac aatcttcgga attgttgtaa cagggctcta tcacagacaa    2640
agaattcatg gagaaggttc tgaaagaaca taagatagaa gttgtaatat ctgcagtggg    2700
agggggaagc atcttagacc agttcaatct gatagaggct atcaggaatg ttgacactgt    2760
caaggtatat gctcaaaaca caactaaca ttcatagggg aagaaactta gatcttgtat     2820
atggtcaatg tagtgacttg tttggtatgt ttgagcttct agttagaata aaacacttat    2880
tgcatgccta gctaaaagtt aggaacttct tttgaaaact agtttagcta gagctaagct    2940
attctaagca agaagacatt aaatagtacc taaagctatg ttttctatt taattcaaca    3000 agcattgcac aaaatgggtt aatgagtcaa aggtgaatct gttgcagagg ttcttaccgt    3060
ctgaattcgg gcacgacaca gacagggctg accggtgga gccagggctg accatgtatg     3120
aacaaaagag gcagattagg aggcagatag agaaatctgg gattccttac acttacatat    3180
gttgcaattc cattgcagct tggccctacc acgacaacac tcaccctgca gatgttctgc    3240 caccctaga taggttcaaa atctacggtg atggcactgt caaaggtacc tcatctttct    3300 ttttccttc attggttttg ttttgtgta tcttgacttt agtgtggttg gtagatggaa     3360
aacgatagca tagaaattg ggaagagaag gatggatgag agattttggt tttccaagaa     3420
aatcaatgtc ccaggatctc tcattaaata accacctccc acatgatatt ccatcttatc    3480
atatcaaagt aaatagatta ctagcatttg tttgcttgag ttttaaatgt cttctattag    3540
aagctaacat tgggaaatta attagaggtc agatcatagg aaaaaatttt aatggttgag    3600
gtaaatgttg cctgcaattt aattctgaca ttggttgagt ttggtgaaac aagaaaaatt    3660
```

```
tgagttaatt agtggtttgt ctctgttgtt tacaaagata gataatactg gatctcttag    3720
tttggctggc aaatattcag cagtcttaca gttttaagaa caaatgctgc ctacctactg    3780
ccatcccatt ttctagtaga agaaggaaga gacaagggac tgaatctttt gaaatgaaaa    3840
aaccaaaaca catgtaaatg attggataag aaaaaatatt agggaaaaaa agaaatagca    3900
gtcatagtca aagtgctgat caggtgtcta gatatataca ggtatagcat gttatattct    3960
agacgaaggc actgtatggc agcaggtata ggcttcaaat aaactttat cttatatggc     4020 ctgctgcttt gacgaaattg aaaatttatc atcaactagg ccaattatcg tttaattcaa    4080
aatagctttc aaactaacct aaatggccat ttcttcaaag ccccgagtaa acctttttgt    4140
cccatctttt tggtagtcga tagtatccac ttcatttggt taatgcaatt atttcattct    4200
aaacatttct gcttcaataa tgacttcctc caaatctgga tagccagaag ggatattttc    4260
taccaaattg gaagctttga actcacaggc gaaaggggt aattttttttt ctaccatgcc    4320 gtaaccagca taatatcatc acaaatccat gatcatattt ttactaaata gatctcatat    4380
ttcatagtat ttcttacagc tctaaaccta ctcattcagc attgtaaaat tgagcagcca    4440
agagagctag tccagcttgt ccttttgata gaggacaaag gagaaagagt cttagtcaaa    4500
gtacaatgca ccctgcttcc tcttttcctt tagtaaaata gtagaagcga caccagttct    4560
aaataggttt tgcatcttgg ctagttccaa gaaatttgct agtcattaag gcaatgcccc    4620
attaggaagg aaaagtcgta agaatcggtg gacctcccct agattcccaa cggatagaat    4680
gatgttttgc ttcttcttc ttgttgttga gcagcactga gaggcacgtg actgctatga     4740
tgggttaggt agcagattat cacgtgaccc catcctctcc taacactttc ccatcccttt    4800
ccttcttttc accccaaca aacacacaaa aagggttatt tattagctac cgggaacatt      4860
acattaaagc atcaagttaa taatagtttg ggaattgaat ttttaaaccct ttgactccgt    4920 cagtttagat ctttcatttt caaattgagt tattaataaa ttattacaaa ataattgaca    4980
taatatagga caacccaatt tacttgggta atcactatat tttaaaggct atgttgttag    5040
gcagcctatt ctaggaggag tcaatgtcga caactggaca tttggggtaa aagaagtcc     5100 aagatttgat cattcatagg ctgtcctaag ctaatcgaaa aggaggaagt cccaactaat    5160 taactgttt ggtaaacaag tttattctca agagaggacc accgaattca tgtcagagat     5220
ttgcttatta attcaaagat ttggactttt ggatgttgcc cgtgagtttc tgacgttggc    5280
tcagagcaag tctttgatct tcttgtcaaa gaaactgctc tacccttcta ataatgagta    5340
aaccagtcac agaaagcaac ccccaggtcc aacctactct tcaacagttt gctagtttaa    5400
aaaaagaaaa agaaaaattg gggtttgcat gtacctaagt taccatctct gcattgaatt    5460
taagttgtag tagtagttgt aaaataaagt ctagaaccaa aagcttttaa tgaaagacaa    5520
cttaggtcca taactcacca tcattatgag aattttgaat atcaatcacc ttactgtata    5580
ttatttatga tgttgactct atgattttgt ggtgaatgcc cagcatactt tgtggcgggt    5640
accgatattg ggaagttcac tataatgtcg atagaagatg atcgaacact gaacaaaact    5700
gtccattttc aacctccaag caacctacta aacataaacg agatggcctc actatgggag    5760
gagaagattg gacgtacact tcctagggtc accatcacag aagaagatct gctgcagatg    5820
gccaaaggtt tgtcctaatt attttcagtt ttctttaagg ttttggttca agcaacttaa    5880
cctttctcca aggaactata tgccactcgg ttggctccat taagcattaa tccatgaagc    5940
agtaagttct tgcctaacaa aatggatgct aacccaactt ctgatataaa tgcagagatg    6000
```

```
cggatcccac agagtgtggt tgcagcatta actcatgata ttttcataaa tggctgccaa      6060
ataaacttta gcttggacaa gccaactgat gttgaagtct gctccctcta cccagacact      6120
ccttttcgaa ccatcaacga gtgcttcgag gactttgcca agaagataat tgataatgcc      6180
aaagcagtga gcaagccagc ggcaagcaac aatgcaatat ttgtgccaac tgctaagcca      6240
ggagcattgc ctatcactgc gatatgcaca tgagaaatat ctcactctat ccatttccac      6300
atcaataatt cttttacaag ttcttttaat cgtacaatgg taagagactt atctgttgcc      6360
agtgtttccg gcaaaaacta atcanatgta tctcttgaat aaatatc                    6407
```

<210> SEQ ID NO 13
<211> LENGTH: 864
<212> TYPE: DNA
<213> ORGANISM: Theobroma cacao

<400> SEQUENCE: 13

```
atgggaaggg ctccttgttg ttctaaagtt gggttgcata gaggtccctg gactcctaga       60
gaagacacat tgcttgtcaa gtacattcaa gctcatggtg acggtcactg gagatcactt      120
cctaagaaag ccgggcttct taggtgtgga agagttgca ggctcagatg gatgaactat        180
ttaagaccag atataaagag agggaatata actcccgatg aggatgatct tatcatcaga      240
ttacattccc tcctcggcaa tcggtggtca ctcattgccg gaaggcttcc tggtcgaacc      300
gataacgaga ttaaaaatta ctggaacacc catctgagta aaagacttct aagccaaggg      360
actgacccta cacccacaa gaaactatca gagcccccag ttcaacaagt gaagaagaga      420
aaaagcagca gaggcaacag caacaagaag cagaacaata gcaagggcaa aggcgcaaag      480
gttgagccag aagagcccaa agtccatctc cctaagcccg ttagagtaac ttctttctct      540
ttaccaagaa acgacagctt tgaccaatgt aatacgttta gcacggtgtc ttcaagccaa      600
ggaggagagg gaggattggg tacagaggtt gtacagggac cttggtcaga taatgtcaac      660
gatgatgaaa atgggaccgg atttcttgct gcttatgatg atcatggttt tgttaacggt      720
tcagatttcg agtgccagtc tcatgtacca gcaagtgatg acgataattc tctcgagaag      780
ctttacgaag agtatctcca gcttctgaag acaaacgatg atcaagtgca gttggattct      840
ttcgctgaat cattattgat ctga                                             864
```

<210> SEQ ID NO 14
<211> LENGTH: 287
<212> TYPE: PRT
<213> ORGANISM: Theobroma cacao

<400> SEQUENCE: 14

```
Met Gly Arg Ala Pro Cys Cys Ser Lys Val Gly Leu His Arg Gly Pro
1               5                   10                  15

Trp Thr Pro Arg Glu Asp Thr Leu Leu Val Lys Tyr Ile Gln Ala His
            20                  25                  30

Gly Asp Gly His Trp Arg Ser Leu Pro Lys Lys Ala Gly Leu Leu Arg
        35                  40                  45

Cys Gly Lys Ser Cys Arg Leu Arg Trp Met Asn Tyr Leu Arg Pro Asp
    50                  55                  60

Ile Lys Arg Gly Asn Ile Thr Pro Asp Glu Asp Leu Ile Ile Arg
65                  70                  75                  80

Leu His Ser Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr His Leu
```

-continued

```
                100                 105                 110
Ser Lys Arg Leu Leu Ser Gln Gly Thr Asp Pro Asn Thr His Lys Lys
            115                 120                 125

Leu Ser Glu Pro Pro Val Gln Gln Val Lys Lys Arg Lys Ser Ser Arg
            130                 135                 140

Gly Asn Ser Asn Lys Lys Gln Asn Asn Ser Lys Gly Lys Gly Ala Lys
145                 150                 155                 160

Val Glu Pro Glu Glu Pro Lys Val His Leu Pro Lys Pro Val Arg Val
                165                 170                 175

Thr Ser Phe Ser Leu Pro Arg Asn Asp Ser Phe Asp Gln Cys Asn Thr
            180                 185                 190

Phe Ser Thr Val Ser Ser Ser Gln Gly Gly Glu Gly Gly Leu Gly Thr
            195                 200                 205

Glu Val Val Gln Gly Pro Trp Ser Asp Asn Val Asn Asp Asp Glu Asn
            210                 215                 220

Gly Thr Gly Phe Leu Ala Ala Tyr Asp Asp His Gly Phe Val Asn Gly
225                 230                 235                 240

Ser Asp Phe Glu Cys Gln Ser His Val Pro Ala Ser Asp Asp Asp Asn
                245                 250                 255

Ser Leu Glu Lys Leu Tyr Glu Glu Tyr Leu Gln Leu Leu Lys Thr Asn
            260                 265                 270

Asp Asp Gln Val Gln Leu Asp Ser Phe Ala Glu Ser Leu Leu Ile
            275                 280                 285
```